(12) United States Patent
Barth et al.

(10) Patent No.: US 8,534,838 B2
(45) Date of Patent: Sep. 17, 2013

(54) OPTICAL COHERENCE REFLECTOMETRY WITH DEPTH RESOLUTION

(75) Inventors: Roland Barth, Jena (DE); Roland Bergner, Jena (DE); Wilfried Bissmann, Jena (DE); Rudolf Murai von Buenau, Jena (DE); Martin Hacker, Jena (DE); Ingo Koschmieder, Jena (DE); Adolf Friedrich Fercher, Vienna (AT); Branislav Grajciar, Bratislava (SK); Ralf Ebersbach, Schmoelln (DE)

(73) Assignee: Carl Zeiss Meditec AG, Jena (DE)

( * ) Notice: Subject to any disclaimer, the term of this patent is extended or adjusted under 35 U.S.C. 154(b) by 236 days.

(21) Appl. No.: 13/059,039

(22) PCT Filed: Aug. 11, 2009

(86) PCT No.: PCT/EP2009/005811
§ 371 (c)(1),
(2), (4) Date: Feb. 14, 2011

(87) PCT Pub. No.: WO2010/017954
PCT Pub. Date: Feb. 18, 2010

(65) Prior Publication Data
US 2011/0149245 A1 Jun. 23, 2011

(30) Foreign Application Priority Data

Aug. 12, 2008 (AT) ................................ A 1250/2008
Oct. 10, 2008 (DE) ......................... 10 2008 051 272

(51) Int. Cl.
*A61B 3/10* (2006.01)
*A61B 3/00* (2006.01)
(52) U.S. Cl.
USPC ............ 351/215; 351/205; 351/221; 351/246

(58) Field of Classification Search
USPC .................................. 351/205, 215, 221, 246
See application file for complete search history.

(56) References Cited

U.S. PATENT DOCUMENTS

| | | | |
|---|---|---|---|
| 5,321,501 | A | 6/1994 | Swanson et al. |
| 5,673,096 | A | 9/1997 | Dorsel et al. |

(Continued)

FOREIGN PATENT DOCUMENTS

| | | |
|---|---|---|
| AT | 506 093 A2 | 6/2009 |
| DE | 44 46 183 A1 | 6/1996 |

(Continued)

OTHER PUBLICATIONS

Bashkansky, M., et al., "Statistics and reduction of speckle in optical coherence tomography," *Optics Letters*, vol. 25, No. 8, pp. 545-547 (Apr. 15, 2000).

(Continued)

*Primary Examiner* — Jack Dinh
(74) *Attorney, Agent, or Firm* — Patterson Thuente Pedersen, P.A.

(57) ABSTRACT

A device for performing distance measurements on an eye. The device includes an interferometer, focuses at least one measurement beam records backscattered radiation and interferometrically generates a measurement signal displaying structures of the eye by time-domain, spectral-domain or Fourier-domain coherence reflectometry, has an adjustment apparatus for laterally and/or axially displacing the focus in the eye or for varying a polarization state of the measurement beam and has a control apparatus which actuates the interferometer, wherein the control apparatus generates a plurality of A-scan individual signals from the backscattered radiation, combines these to an A-scan measurement signal and actuates the adjustment apparatus for displacing the position of the focus or for varying the polarization while recording the backscattered radiation from which the control apparatus generates the A-scan individual signals is being recorded.

22 Claims, 10 Drawing Sheets

(56) References Cited

U.S. PATENT DOCUMENTS

| | | |
|---|---|---|
| 5,847,827 A | 12/1998 | Fercher |
| 6,057,920 A | 5/2000 | Fercher et al. |
| 6,267,477 B1 | 7/2001 | Karpol et al. |
| 6,806,963 B1 | 10/2004 | Waelti et al. |
| 6,922,250 B2 | 7/2005 | Fercher |
| 7,084,986 B2 | 8/2006 | Hellmuth et al. |
| 7,322,699 B2 | 1/2008 | Barth et al. |
| 7,370,968 B2 | 5/2008 | Hanebuchi |
| 7,695,137 B2 | 4/2010 | Fercher |
| 2005/0203422 A1 | 9/2005 | Wei |
| 2006/0109477 A1 | 5/2006 | Zhou et al. |
| 2006/0195076 A1 | 8/2006 | Blumenkranz et al. |
| 2007/0076217 A1 | 4/2007 | Baker et al. |
| 2007/0291277 A1 | 12/2007 | Everett et al. |
| 2008/0002211 A1 | 1/2008 | Park et al. |
| 2008/0285043 A1 | 11/2008 | Fercher et al. |
| 2010/0284021 A1 | 11/2010 | Hacker |

FOREIGN PATENT DOCUMENTS

| | | |
|---|---|---|
| DE | 198 14 070 A1 | 10/1999 |
| DE | 10 2007 052 828 A1 | 5/2008 |
| DE | 10 2007 027 683 A1 | 12/2008 |
| DE | 10 2007 046 507 A1 | 4/2009 |
| WO | WO 97/30627 | 8/1997 |
| WO | WO 01/38820 A1 | 5/2001 |
| WO | WO 03/086180 A2 | 10/2003 |
| WO | WO 2006/074469 A2 | 7/2006 |
| WO | WO 2007/065670 A2 | 6/2007 |
| WO | WO 2007/100935 A2 | 9/2007 |
| WO | WO 2008/151821 A1 | 12/2008 |

OTHER PUBLICATIONS

Hasegawa, M., et al., "Development of a high speed and deep scanning optical coherence tomography system," *CLEO/Pacific Rim 2003, The 5$^{th}$ Pacific Rim Conference on Lasers and Electro-Optics*, vol. 1, Issue 15-19, p. 305 (Dec. 2003).

Drexler, Wolfgang, et al., "Submicrometer Precision Biometry of the Anterior Segment of the Human Eye," *Investigative Ophthalmology & Visual Science*, vol. 38, No. 7, pp. 1304-1313 (Jun. 1997).

Lexer, F., "Wavelength-tuning interferometry of intraocular distances," *Applied Optics*, vol. 36, No. 25, pp. 6548-6553 (Sep. 1, 1997).

Schmitt, Joseph M., "Optical Coherence Tomography (OCT) A Review," *IEEE Journal of Selected Topics in Quantum Electronics*, vol. 5, No. 4, pp. 1205-1215 (Jul./Aug. 1999).

Fercher, A.F., "Measurement of intraocular distances by backscattering spectral interferometry," *Optics Communications*, vol. 117, pp. 43-48 (1995).

de Boer, Johannes F., "Polarization Effects in Optical Coherence Tomography of Various Biological Tissues," *IEEE Journal of Selected Topics in Quantum Electronics*, vol. 5, No. 4, pp. 1200-1204 (Jul./Aug. 1999).

Schmitt, J.M., et al., "Speckle in Optical Coherence Tomography," *Journal of Biomedical Optics*, vol. 4, No. 1, pp. 95-105 (Jan. 1999).

Jørgensen, Thomas M., "Speckle reduction in optical coherence tomography Images of human skin by a spatial diversity method," *Proc. of SPIE-OSA Biomedical Optics, SPIE*, vol. 6627, 5 pgs. (2007).

Yun, S.H., et al., "Motion artifacts in optical coherence tomography with Frequency-domain ranging," *Optics Express*, vol. 12, No. 13, pp. 2977-2998 (Jun. 28, 2004).

OPTICAL COHERENCE REFLECTOMETRY WITH DEPTH RESOLUTION

PRIORITY CLAIM

The present application is a National Phase entry of PCT Application No. PCT/EP2009/005811, filed Aug. 11, 2009, which claims priority from Austrian Application Number A 1250/2008, filed Aug. 12, 2008, and German Application Number 102008051272.9, filed Oct. 10, 2008, the disclosures of which are hereby incorporated by reference herein in their entirety.

FIELD OF THE INVENTION

The invention relates to an apparatus for performing measurements on an eye, in particular for measuring ocular distances such as a depth of an anterior chamber, a lens thickness, a corneal thickness or an axial length, wherein the apparatus comprises an interferometer, focuses at least one measurement beam into the eye along an optical axis, collects back-scattered radiation and interferometrically generates a measurement signal indicating structures of the eye by time-domain, spectral-domain or Fourier-domain coherence reflectometry, and has an adjustment device for laterally and/or axially shifting the focus in the eye or for varying a polarization state of the measurement beam, and has a control device, which controls the interferometer. The invention relates further to a method for performing measurements on an eye, in particular for measuring ocular distances such as a depth of an anterior chamber, a lens thickness, a corneal thickness or an axial length, wherein at least one measurement beam is focussed into the eye along an optical axis, back-scattered radiation is collected and a measurement signal indicating structures of the eye is generated interferometrically by time-domain, spectral-domain or Fourier-domain coherence reflectometry, and the position of the focus in the eye is shifted laterally and/or axially or a polarization state of the measurement beam is varied.

Today, axial eye lengths and intraocular distances are measured by means of optical short-coherence interferometry (SCI). Compared with the previously prevailing ultrasound method, optical short-coherence interferometry has the advantages of the contactless and high-precision method of operation. The eye in this case is located in the measurement arm of a short-coherence interferometer, which, for example, is a dual-beam interferometer illuminated by light of short coherence length. In this case, a (short-coherence) interferogram is produced at the output of the interferometer only if a structure that reflects or backscatters light is present in the measurement arm at precisely the same optical distance from the beam splitter as the reference mirror, except for the coherence length; this region is frequently referred to as a "coherence window". The coherence window has an extent in the beam direction of the magnitude of the coherence length, which, in the case of short-coherence methods, is usually only a few micrometers. In the case of the so-called "short-coherence scan", the eye is scanned from the coherence window by displacing the reference mirror in the beam direction along the axis of vision (z direction or object depth). If a light-remitting location of the eye is present in the coherence window, a short-coherence interferogram is produced at the output of the interferometer, as already stated. The movement of the reference mirror required for this constitutes the measuring operation; the distances of limiting surfaces to be measured are marked at the output of the interferometer by the short-coherence interferograms assigned to the respective limiting surfaces, along the reference mirror path z. By analogy with similar methods in the ultrasound technique, this sequence of short-coherence interferograms having the z-dependent backscatter intensity I(z) is called the "A-scan" signal.

Optical coherence domain reflectometry (OCDR), or also called short coherence interferometry (SCI), serves to acquire the location and magnitude of scattering centres within a specimen, e.g. the human eye. Reference is to be made to US 2006/0109477 A1 for an overview of corresponding literature concerning optical coherence domain reflectometry. This patent application also describes the basic principle of imaging optical coherence tomography (OCT). For OCDR, the variants time-domain OCDR (time-domain or TD OCDR), with a reference arm adjusted in respect of path length for scanning, and Fourier-domain OCDR (FD OCDR/FD SCI), with a fixed reference arm and evaluation of spectral information, are known. The latter is again differentiated into a variant using broadband light sources and spectrometer-based detection (spectral domain or SD OCDR) and into a variant using spectrally tunable light sources and broadband detectors (swept-source or SS OCDR).

In the case of the more sensitive Fourier-domain short coherence interferometry (FD SCI), the light emerging at the output of the interferometer is analyzed by a spectrometer; under appropriate conditions, which are known in the state of the art (U.S. Pat. No. 7,330,270 B2), a Fourier transformation (FT) is used to obtain from the measured intensity spectrogram I(k) the reconstructed A-scan signal in the z direction along the illuminating measurement beam:

$$r(z)=FT\{I(k)\} \quad (1)$$

wherein the wave number $$k = \frac{2\pi}{\lambda} n,$$

c is the speed of light, $\lambda$ is the wavelength, n is the respective refractive index and r(z) is the scattering amplitude, the squared value of which corresponds to the scatter intensity I(z).

A problem for short coherence interferometry in the form of FD OCDR and FD OCT is the fixed association between the measurement region and the measurement resolution. The state of the art includes many publications dealing with the measuring of objects in regions that are geometrically larger, by several orders of magnitude, than the desired resolution. An example of such a measurement task is the measuring of regions on the human eye, e.g. the detection of structures both in the anterior region of the eye, for example on the cornea, and on the retina.

In the case of OCDR, the axial and the lateral resolution are mainly independent from each other. The axial resolution is given substantially by the coherence length of the source, i.e. inversely proportional to the total width of the spectrum used in the interferometer arrangement. In the lateral direction, the achievable resolution is given by the lateral extent of the focus, or of the beam waist in the focal region. The scatter signal of a site is thus the superposition of the radiation back-scattered out of the smallest resolvable volume.

An application that is of particular interest for the OCDR technique is that of distance measurement in the eye. At present, known appliances that operate interferometrically make it possible to achieve either a satisfactory axial length measurement or a partial distance measurement in the anterior chamber, e.g. acquisition of the anterior chamber depth and of the lens thickness. For the individual partial distance measurements in this case, the measurement beam has to be adjusted with great precision in the eye.

Known methods for partial distance or axial length measurement work along the axis of vision of an eye (e.g. Lexer et al., "Wavelength-tuning interferometry of intraocular distances", APPLIED OPTICS, Vol. 36, No. 25). For partial distance measurements, therefore, they generally do not use the strong and clearly defined specular reflexes from limiting surfaces in the eye, which reflexes can be detected on the optical axis of the eye, but utilize signals from volume scatterings in structures of the eye.

SUMMARY OF THE INVENTION

In order to obtain optimal signals, there are some requirements that have to be fulfilled in the case of in vivo measurements on the eye and that apply in part to both short-coherence interferometry methods (FD OCDR and TD OCDR). They include:

1. Adaptation of the intensity ratio between the measurement beam and reference beam.
2. Multiple reference beams, owing to limited depth of field (FD SCI).
3. Short measurement times.
4. Adaptation of intensity to reflectivities of the eye structures.
5. Identifiability of the eye structure associated with the signals registered.

Concerning 1. This applies to TD SCI and FD SCI for the purpose of optimizing the sensitivity.

Concerning 2. The Fourier-domain short coherence interferometry—in the case of currently standard detector arrays—has a measurement depth of field T that is limited to a few millimeters.

$$T = N \cdot \pi / \Delta K \quad (2)$$

wherein N=is equal to the number of scanning points (~ number of detector array elements in the $\lambda$ direction); $\Delta K$ is the spectral width $\Delta\lambda$ of the measurement light, expressed as a width of the scattering vector $K=4\cdot\pi/\lambda$. That is usually sufficient for measuring the corneal thickness and, depending on the spectral width of the measurement light, also for measuring the depth of the anterior chamber. With arrays that are currently commercially available, measurements of eye lengths can be performed only with a very low depth resolution (small spectral width of the measurement light). In the case of FD-SCI, therefore, it is necessary to realize two measurement fields at differing depths, by means of two reference beams or two sample beams.

Concerning 3. For measurement of eye length, however, in order to achieve an unambiguous distance measurement it is necessary, owing to the natural motion of the (living) eye, that both short-coherence interferograms marking the distance to be measured be recorded simultaneously or very closely in time, which is not easily achievable in the case of the FD-SCI with the depth of field limited to a few millimeters, since the reference mirror defining the position of the measurement field would first have to be displaced to enable the second signal also to be seen. An expedient consists in realizing a second measurement field in the required depth position by means of a second reference beam. FD A-scan signal pairs are thus obtained, from whose short-coherence interferograms it is possible to determine the distance of interest, taking account of the path difference of the reference beams.

In the case of TD SCI, again, the two measurement positions cannot be acquired simultaneously, owing to the necessary movement of reference mirrors. To enable the time interval between the two measurement positions to be reduced in this case, likewise, two reference beams, which realize two coherence windows, can also be used here. In order to obtain a plurality of laterally offset A-scan signals, the measurement beam can be displaced laterally, as is usual, by means of a mirror device. A-scan signals of the eye structures, relevant to length measurement, that are transversally offset in relation to one another can be obtained much more rapidly, however, by means of parallel SCI, wherein anamorphic optics based on cylindrical lenses focus the measurement beam into the planes of the relevant eye structures in a linear manner and, by means of the detector array at the output of the interferometer, select the transversally adjacent A-scan signals within this line focus.

Concerning 4. Adaptation of intensity to reflectivities of the eye structures. The reflectivity of the cornea is about $10^3$ times greater than that of individual retinal layers. In order that reflexes of the retinal layers do not become lost in the A-scan signal in comparison with the corneal signal, it is useful for these structures to be illuminated with greater beam intensity than the cornea.

Concerning 5. In the case of both short coherence interferometry methods, the A-scan is effected approximately along the axis of vision, through the eye. In this case, light reflexes, which form the basis for the distance measurement, occur at pronounced tissue boundaries, such as the corneal anterior surface and the fundus layers. However, light reflexes and measurement signals also occur at structures that are not correctly identifiable; erroneous measurements are the result.

FIG. 14 describes examples relating to this:

A-scan #1 shows, in the measurement window F1, a strong signal at the cornea (C) and, in the measurement window F2, a strong signal at the inner limiting membrane (IG) and no signal from the retinal pigment epithelium (RP); an erroneous measurement is obtained.

A-scan #2 shows a weak signal at the cornea (C), a weak signal at the inner limiting membrane (IG), and no signal from the retinal pigment epithelium (RP); an erroneous measurement is obtained.

A-scan #3 and 4 show a strong signal at the cornea (C), no signal at the inner limiting membrane (IG), and a strong signal from the retinal pigment epithelium (RP); a correct measurement is obtained.

A-scan #5 shows a strong signal at the cornea (C), a weak signal at the inner limiting membrane (IG), and no signal from the retinal pigment epithelium (RP); an erroneous measurement may be obtained.

A-scan #6, 8 and 9 show a strong signal at the cornea (C), a weak signal at the inner limiting membrane (IG), and a strong signal from the retinal pigment epithelium (RP); a correct measurement is obtained.

A-scan #7 shows a weak signal at the cornea (C), a strong signal at the inner limiting membrane (IG), and a weak signal from the retinal pigment epithelium (RP); an erroneous measurement is probably obtained.

The invention is therefore based on the object of enabling an eye, and in particular a distance, to be measured in an improved manner by means of time-domain spectral domains or Fourier-domain coherence reflectometry. Particularly preferably, an axial length measurement and a further sub-full-distance measurement are to be performed on the eye at the same time. The signal-to-noise ratio and, in particular, the capacity for limiting-surface determination on the basis of volume scattering signals are to be improved, measurement errors are to be prevented and the requirements for adjustment of the eye are to be reduced.

This object is achieved, according to the invention, by an apparatus for performing measurements on an eye, in particular for measuring a depth of an anterior chamber, a lens thickness, a corneal thickness or an axial length, and measuring retinal layer thicknesses such as, for example, the thickness of the nerve fibre layer or the distance between an inner limiting membrane (ILM) and a retinal pigment epithelium (RPE), wherein the apparatus comprises an interferometer, focuses at least one measurement beam into the eye along an optical axis, collects back-scattered radiation and interferometrically generates a measurement signal indicating structures of the eye by time-domain, spectral-domain or Fourier-domain coherence reflectometry, and has an adjustment device for laterally and/or axially shifting the focus in the eye or for varying a polarization state of the measurement beam, and has a control device, which controls the interferometer, wherein the control device generates a plurality of A-scan individual signals from the back-scattered radiation, combines these to form an A-scan measurement signal and is designed such that it controls the adjustment device for shifting the position of the focus or for varying the polarization during collection of the back-scattered radiation from which the control device generates the A-scan individual signals, and wherein back-scattered radiation contributes to the A-scan measurement signal in a plurality of differing positions of the focus or in a plurality of differing polarization states of the measurement radiation.

The object is further achieved, according to the invention, by means of a method for performing measurements on an eye, in particular for measuring a depth of an anterior chamber, a lens thickness, a corneal thickness or an axial length, wherein at least one measurement beam is focussed into the eye along an optical axis, back-scattered radiation is collected and a measurement signal indicating structures of the eye is generated interferometrically by time-domain, spectral-domain or Fourier-domain coherence reflectometry, and wherein the position of the focus in the eye is shifted laterally and/or axially or a polarization state of the measurement beam is varied, wherein a plurality of A-scan individual signals are generated interferometrically from the back-scattered radiation and combined to form an A-scan measurement signal, wherein the shifting of the position of the focus or the variation of the polarization state is performed during the collection of the back-scattered radiation from which the plurality of A-scan individual signals are generated, and wherein back-scattered radiation contributes to the A-scan measurement signal in a plurality of differing positions of the focus or in a plurality of differing polarization states of the measurement radiation.

The object is furthermore achieved, according to the invention by cumulative A-scan signals, which are obtained as a sum of a plurality of individual A-scan signals that are laterally offset in relation to one another, or as a sum of a plurality of individual A-scans at the same location that succeed one another in time, or as a sum of a plurality of individual A-scan signals that are laterally offset in relation to one another and succeed one another in time, or as a sum of a plurality of individual A-scan signals that are laterally offset in relation to one another within a surface, or as a sum of a plurality of individual A-scan signals that are laterally offset in relation to one another within a surface and succeed one another in time, or as a sum of a plurality of individual A-scan signals from particular transversal positions in the eye and at particular instants within the cardiac pulse period.

Frequently, in the case of OCDR interferometers, the focus of the measurement radiation also corresponds to the region, in particular the focus, from which the back-scattered radiation is collected.

The invention achieves an improved signal-to-noise ratio for the A-scan measurement signal in that the latter is composed of a plurality of A-scan individual signals, wherein the focus position and/or the polarization state of the measurement radiation is altered during the collection of the radiation for the A-scan individual signals. The A-scan individual signals therefore differ in respect of the focus position or the polarization state of the measurement radiation.

Thus, according to the invention, back-scattered radiation, which has been obtained at differing focus positions or in differing polarization states of the measurement radiation, contributes to the A-scan measurement signal. The apparatus and the method thus generate an A-scan measurement signal that contains information about the backscattering strength and location of back-scattered structures of the eye, wherein the location is given in the depth direction. The term A-scan in this case is to be understood in the manner that is usual in ophthalmology. The A-scan supplies data along the eye, i.e. from posterior to anterior. In the meaning of the present invention, an A-scan signal is a signal that represents the backscatter intensity of structures of the eye along the depth direction of the eye.

The invention now combines a set of a plurality of A-scan individual signals to form a individual A-scan measurement signal, wherein the A-scan individual signals of the set differ from one another in respect of the position of the focus or of the polarization state of the measurement radiation that was injected to obtain the A-scan individual signal. As a result, the invention achieves a single A-scan measurement signal, which has been generated from measurement radiation having a mixture of differing focus positions or polarization states. The alteration of focus position or polarization state in this case does not necessarily have to be performed to the full extent of alteration during the pick-up of the back-scattered radiation for one of the plurality of A-scan individual signals. Rather, it is expedient for the full extent of alteration to be distributed over one or more sets.

The variation of the focus position or of the polarization state of the measurement radiation during the pick-up of back-scattered radiation utilized for generating the A-scan individual signals does not have to continue to be effected in a synchronized manner to generate the A-scan individual signals. In this, apart from the fact that a plurality of A-scan individual signals are combined to form a common A-scan measurement signal, there is a further difference from usual imaging methods, which necessarily depend on a synchronization between focus position adjustment and signal generation. The absence, in a variant of the invention, of synchronization between variation of focus position or polarization and generation of the A-scan individual signals becomes apparent through a variation of the phase between the variation of focus position or polarization and the pick-up of the back-scattered radiation for generating A-scan individual signals. There is no rigid phase relationship between these two operations; rather, the phase varies. This becomes particularly clear in the variant mentioned, in that the phase position at the start of the pick-up varies from set to set of the plurality of A-scan individual signals that are then combined to form an A-scan measurement signal (i.e. for differing sets of A-scan individual signals). Thus, if the apparatus, or the method, generates a plurality of A-scan measurement signals in succession, wherein each A-scan measurement signal is generated from a set of successively picked-up A-scan individual signals, the same phase for varying the focus position or polarization state is not present at the start of each set. This advantageous feature of the invention allows the use of a simple structure for varying the focus position or the polarization state, since there is no need for feedback between the variation and the pick-up of the back-scattered radiation for the A-scan individual signals. The variation can be performed, for example, by means of a free-running oscillator, and continuous measurement or determination of the current focus position or of the current polarization state is not applicable, or is not performed in the method or by the control device.

The inventors identified that an improvement in the signal-to-noise ratio and the prevention of measurement errors of the A-scan measurement are preferably achieved without the current focus shift or polarization variation of the measurement radiation being taken into account, which leads to a considerably simplified structure and a considerably simplified method. The focus shift or polarization variation is preferably not considered when combining the A-scan individual signals to form the A-scan measurement signals. Thus, in order to limit the equipment requirement to a small amount, imaging is not necessarily effected.

The concept according to the invention makes it possible, in a simple manner, to suppress various effects that can reduce the signal-to-noise ratio or produce measurement errors. The invention can therefore be developed further, particularly advantageously, for the purpose of distance measurement on the eye, since limiting surfaces that delimit the distance can be better acquired. It is therefore provided, in a development of the invention, that the control device performs a distance measurement on the eye. This applies analogously to the method according to the invention.

In the case of the OCDR used according to the invention, the backscatter signal of a site in the eye is obtained through the superposition of the radiation back-scattered out of the smallest resolvable volume. In this case, the individual radiation components can interfere in all stages between constructive or destructive, depending on the structure of the eye within the smallest resolvable volume. As a result, speckles are obtained, which may be brighter or darker, depending on the nature of the interference (constructive or destructive). Such speckles are produced as a result of the interfering superposition of the sites from the specimen volume resolved by the measurement method used, and are known per se from the field of ultrasound and OCT measurements (J. M. Schmitt, "Optical Coherence Tomography (OCT): A Review", IEEE Selected Topics in Quantum Electronics, Vol. 5, No. 4, pp. 1205-1215, 1999). Their minimum size is determined laterally by the focus size and axially by coherence length as a result of the source bandwidth used. Although these speckle modulations contain items of information about the specimen, are actually part of the backscatter signal and are also predominantly temporally stable, i.e. are not noise in the actual sense, they nevertheless constitute a problem for determinations of limiting surface and determinations of distance based thereon that is at least as great as inadequate signal-to-noise ratios. For this reason, speckle modulations are considered here to belong to noise, and not to signal, and their prevention is interpreted as an improvement of the signal-to-noise ratio.

In the case of reconstruction of signal amplitudes, in addition to dark speckles, bright speckles, having differing amplitude signs, are also possible because of the phase information contained in the speckles. In the case of distance measurement on the eye, an error occurs if a limiting surface to be taken into account for the distance measurement locally exhibits a dark speckle, i.e. such a speckle having amplitudes less than that of the statistical noise components. This limiting surface is then incorrectly detected, and a measurement error in the distance measurement is the result. The invention variant with a lateral specimen shift now ensures that it is not exclusively A-scan individual signals based on a dark speckle that are included in the formation of the A-scan measurement signal; rather, the combination of A-scan individual signals that have been obtained at differing lateral positions of the focus automatically ensures that bright speckles also contribute to the formation of the A-scan measurement signal, such that the aforementioned measurement error is prevented. The axial error, caused by the lateral variation of position, in the case of the determinations of limiting surfaces on the predominantly flat eye structures is then significantly smaller than that which would result from an erroneous measurement at a dark speckle.

An example is the boundary surface of the lens. The posterior lens radius, having a typical mean value of 6 mm, is one of the most curved structures on the eye. A usual lateral focus diameter in ophthalmological appliances is, for example, 25 µm. If a lateral positional variation were then to be performed, for example over four lateral speckle diameters, or 100 µm, during the pick-up of A-scan individual signals, this would correspond to an axial positional alteration of the limiting surface by less than 1 µm. With use of OCDR methods having usual axial resolutions of 10 to 20 µm, however, the measurement error resulting from a potential erroneous measurement at a dark speckle would be greater by at least one order of magnitude.

In the case of distance measurements in the eye, it is necessary that the boundary surfaces confining the distances be acquired with an adequate signal-to-noise ratio. If the A-scan measurement signal is generated from A-scan individual signals that differ in respect of the axial focus position, these A-scan individual signals in their totality will represent the same specimen structure, namely, that specimen structure with which measurement depth defined by the interferometer is accessible, but backscattering structures are nevertheless present, which are focally more distant and then have a lesser intensity in an A-scan individual signal than specimen structures that are focally closer. The axial displacement of the focus during the pick-up of the radiation for the A-scan individual signals, provided in a further variant of the invention, therefore automatically ensures that a set of A-scan individual signals in which individual specimen structures show signals of differing intensity is present for generating the A-scan measurement signal.

For both variants, it is not necessary for the current position of the focus displacement to be assigned to the A-scan individual signals but, rather, it suffices entirely for the A-scan individual signals to be combined to form the A-scan measurement signal, with merely an addition or averaging, particularly of signal absolute values, resulting in an improved signal-to-noise ratio for all specimen structures within the acquired measurement region.

For distance measurement on the eye, the following structures are usually of particular interest: anterior and posterior surface of the cornea of the eye, anterior and posterior surface of the eye lens and layers of the retina, in particular the ILM (inner limiting membrane) and the RPE (retinal pigment epithelium). The invention can be used, in combination with a method or an apparatus whose measurement depth allows a direct measurement of the desired distances, e.g. the total length of the eye, to measure distances derived from these limiting surfaces. Axial shifting of the focus during the measurement is particularly advantageous for such an application. Optionally, however, the invention can also be realized with an apparatus or a method that acquires a partial portion of the eyes in a first measurement state and acquires a second partial portion of the eye in a second measurement state. The lateral or axial shifting of the focus then occurs at least in one of the measurement states.

A further aspect that can result in measurement errors in distance measurements on the eye lies in the fact that the eye has to be appropriately aligned to the apparatus or for the measurement process. The term adjustment state is used here. Sometimes, however, an adequate adjustment state becomes lost again even, before the start of the actual measurement, owing to a movement by the patient, and an adjustment process has to be performed again. Clearly, this constitutes a loss of time. In addition, there is the risk that the loss of the adequate adjustment state is identified too late, and an invalid measurement is therefore performed. In respect of the lens of the eye, the adjustment state is optimal when the lens is as perpendicular as possible to the incident measurement radiation, since a strong specular back-reflex is then produced. As is known, in the case of the human eye, the optical axis through the lens and the axis of vision through the centre of most acute vision, the fovea centralis, differ from one another by 0 to 14°, typically by 5°, such that the lens is tilted relative to the axis of vision. If a patient is then made to fix the gaze to a fixing object, the result of this is that measurement radiation that is incident on the axis of the image of the fixing object is generally incident upon an tilted lens, and the specular (i.e. mirror-type) back-reflex component that is detectable in the direction of the measurement radiation axis is small. An adjustment state that is good for measurement exists when the axis of vision is tilted through displacement of the fixing object, by the differential angle between the axis of vision and the optical axis, such that measurement radiation enters the eye along the optical axis of the lens, and is therefore incident upon a lens that is perpendicular to the direction of incidence, and produces a strong, predominantly specular type back-reflex as a result. Should one wish to determine both the position of the lens and the eye length, i.e. the distance between the corneal vertex and the fovea, in the state of the art either a sequence of two measurements, with intermediate refixing of the patient's gaze, is unavoidable, or it is necessary to accept a weaker reflex at the lens. The invention now resolves this conflict in that, with a lateral shift of the focus, at least in the region of the lens, a strong back-reflex is always ensured, since the lateral drift of the focus in relation to the lens also illuminates lens regions that are more perpendicular to the direction of incidence of the measurement region than is the case in the region of the axis of vision. Consequently, there is no need to refix the patient's gaze, and the design conflict that is present in the state of the art is eliminated. Particularly preferred, therefore, is an embodiment of the invention wherein a distance measurement is performed on the eye and, in this case, both the position of the retina and of the lens is acquired. Again, in this case, it is possible to use an apparatus or a method whose measurement depth overlaps in the distance between the lens and the retina, or it is possible to switch over between measurement of the lens position and of the retina position. Optionally, a dual-beam method is obviously also possible, wherein the lateral shift of the focus is effected at least on the measurement beam for the lens region.

As a result, the invention makes it possible to reduce errors that have been associated with the adjustment state of the eye hitherto necessary in the state of the art.

Owing to the known double-refracting effect of certain eye structures, such as the cornea or the lens or various retinal layers, alteration of the disturbing speckle modulation present in the measurement signals can also be effected through alteration of the polarization state of the incident measurement radiation. In addition, the double refraction can also disturb, or reduce, the interference capacity, and therefore the detectability, of the back-scattered light, such that the variation of the polarization state of the measurement radiation achieves higher individual signals. For the purpose of improving the signal, therefore, it is also provided in the invention that the polarization state of the measurement radiation is varied during the pick-up of the A-scan individual signals. The above statements relating to the lack of necessity of synchronization also apply to this variant.

In the combining of the A-scan individual signals to form the A-scan measurement signal, an improvement of the overall signal is achieved, in comparison with the A-scan individual signals. As mentioned, the combining can be effected, quite fundamentally, by way of addition or averaging. A further improvement is obtained if the A-scan individual signals are selected and weighted. For this purpose, the signal characteristic of the A-scan individual signals is evaluated accordingly. For example, it is possible to make selections of maxima. Since all A-scan individual signals cover the same measurement range, it is possible, for example, to extract the maximum peaks from each of the A-scan individual signals, and to combine these peaks to form the A-scan measurement signal. Threshold value selections can also be made.

The lateral shift of the focus can be achieved in differing ways, e.g. through an appropriate controlled deflection element in the optical structure of the arrangement, which element deflects the measurement beam. Parts that are moved to shift the beam path of the measurement beam are not required if a fixing image presented to the patient is displaced for the purpose of laterally shifting the focus. The set-up is then correspondingly simple, particularly if the fixing image is generated by means of a display that is controllable by the control device and is appropriately controlled to displace the fixing image.

A further variant, relatively simple in respect of equipment, for shifting the focus consists in designing an optical element, e.g. a lens, so as to be adjustable and adjusting it for the purpose of shifting the focus. For an axial shift, an alteration of focal length or an axial positional alteration of a refractive element (for example, a liquid lens or a liquid crystal modulator) or of a reflective optical system (deformable mirror) is effected; for a lateral shift of the focus, the lens is adjusted transversely along to the optical axis.

A further variant does not require any additional elements: depending on a random position and orientation of the eye, which can be altered by involuntary body and eye movements, the A-scan signal of the inner limiting membrane now dominates, for example at the fundus, over the signal from the retinal pigment epithelium (RPE), which is relevant to measurement of length; for example, as indicated by the A-scan signals #1 and #7 in FIG. 14. In addition, random interferences (speckles) of light from scattering centres close behind or in front of the signal can cancel or reduce the individual resultant A-scan short-coherence interferograms. If A-scan signals of these structures are then considered in the local lateral surroundings and/or temporal sequence, it is possible to become independent of such contingencies, and the correct association is found. In particular, a summation of the spatially and/or temporally closely adjacent signals can average out such contingencies. In this case, the spatially transversally offset A-scan signals do not in any way have to produce an image that allows recognition of the transversal anatomical structures; rather, it suffices to pick up such a number of A-scans from the fundus that, for example, two measurement signals, separated by approximately the retinal thickness of about 0.3 mm, are seen in the region of the fundus. Alternatively, the individual A-scan signals can be added up, and the strength of the cumulative signals taken as a basis. At the fundus, for example, the A-scan signal from the retinal pigment epithelium is usually the strongest signal, and therefore is also dominant in the cumulative signal. This is also shown by FIG. 14: if the signals belonging respectively to IG and RP are added up, the sum of RP dominates over that of IG.

For embodiments in which the interferometrically accessible measurement range cannot simultaneously acquire all limiting surfaces that are relevant in the distance measurement, it is preferred that, in addition to the adjustment of position during the pick-up of the back-scattered radiation, the focus also be adjusted to differing, axially spaced-apart partial regions of the object, and that the shift of the focus during the pick-up of the radiation be performed in at least one of the partial regions. This is an example of the previously mentioned measurement states.

In the case of a lateral shifting of the focus, it is advantageous for this to be performed at a shifting speed that is less than the quotient of half the focus diameter and a duration of pick-up of the radiation for an A-scan individual signal, and this shifting speed has proved to be particularly advantageous for reducing the described speckle-induced errors. It is particularly preferred that the quotient be less than 10% of the ratio of the focus diameter and the duration of pick-up of the radiation for an A-scan individual signal.

The embodiments of the invention do not require to know or even do not know the actual shift of the focus for the separate A-scan individual signals. Nevertheless, the invention makes it possible to obtain further information about the eye lens, in that the positions of the lens anterior surface and posterior surface are determined for all individual signals. Thus, a pair of positions of the lens anterior surface and positions of the lens posterior surface is present for each individual signal. The difference between the most anterior determined position of the lens anterior surface and the most posterior determined position of the lens posterior surface represents the thickness of the eye lens.

If the pairs of ascertained position of the anterior lens surface and ascertained position of the posterior lens surface are plotted on a diagram, wherein the position of the anterior lens surface is plotted along one diagram axis and the position of the posterior lens surface is plotted along the other diagram axis, combination or interpolation of the obtained points to form a curve makes it possible to determine a measurement for the tilt of the lens relative to the axis of vision, through evaluation of the maximum distance of the curve points from a symmetry axis of the curve.

The two above-mentioned embodiments are examples of the fact that, even without assignment of the current focus displacement, or of the current polarization state, more extensive information about the eye can be obtained from the A-scan individual signals.

It is understood that the features mentioned above and those that remain to be explained in the following can be applied, not only in the specified combinations, but also in other combinations or singly, without departure from the scope of the present invention.

BRIEF DESCRIPTION OF THE DRAWINGS

The invention is explained by way of example in the following with reference to the appended drawings, which also disclose features essential to the invention. There are shown in.

DETAILED DESCRIPTION

In the interferometric measurement of axial scatter profiles, such as that occurring in the case of optical coherence domain reflectometry, the axial resolution, i.e. the resolution in the depth direction, is given substantially by the coherence behaviour of the source. The resolution is inversely proportional to the total width of the spectrum used for measuring the scatter profile. Transversely in relation thereto, i.e. in the lateral direction, the achievable resolution is given by the lateral extent of the focus, which is referred to here as the focus diameter. In fact, of course, a beam waist is present, and the focus diameter is usually understood to be that size of the beam waist at which the radiation intensity has decreased to a particular value, e.g. $1/e^2$.

The radiation back-scattered from a point on an object is the superposition of the radiation components back-scattered out of the resolved volume. These radiation components can interfere in all stages between constructive and destructive, as a result of which known speckles form. In the case of a constructive interference, bright speckles are present, dark speckles being present in the case of a destructive interference. Whether a constructive or a destructive interference occurs depends on the object structure within the resolved volume. Further, the intensity of the back-scattered radiation depends on how close an object structure is to the focus of the measurement radiation. Object structures that are more distant from the focus result in lesser backscatter intensities, and consequently in less strong interference signals. A further variation of the interference signal strength can occur as a result of double refraction effects in the specimen.

Figure 1:
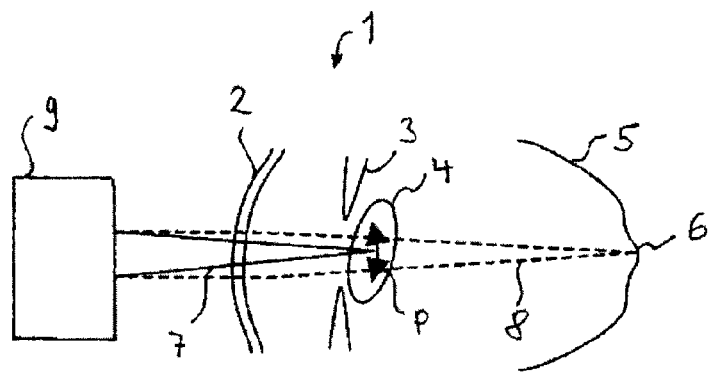
FIG. 1 is a schematic drawing of an apparatus for measuring distances on the eye.

In order now to maximize the signal of a limiting surface to be measured in the case of interferometric object measurement, the focus is shifted or the polarization state of the measurement beam is altered during the measurement of an axial scatter profile, according to FIG. 1. By analogy with the ultrasound measuring technique, such axial scatter profiles are also referred to as A-scans, for which reason the term A-scan measurement signal is used here. A reduction of the interference signal, and thereby of the measurement signal, by a random dark speckle on the object structure is prevented in that the focus is shifted laterally during the measurement. A maximizing of the signal in respect of the distance from the focus is achieved in that the focus is shifted axially during the measurement. Double refraction effects that negatively affect the signal intensity are prevented in that the polarization state of the measurement beam is altered during the measurement.

FIG. 1 shows a section through an eye 1, of which the cornea 2, the iris 3, the lens 4, the retina 5 and the fovea 6 are shown in an exemplary, schematic manner. In the state represented in FIG. 1, the eye is measured by means of two measurement beams 7 and 8. The measurement beam 7 is focussed into the lens 4, and the measurement beam 8 is focussed on the fovea 6. The measurement beams 7 and 8 originate from a measuring apparatus 9, which is designed for optical coherence domain reflectometry (OCDR), and thus effects a depth resolution of the acquired regions, in this case the lens 4 and the retina 5. In respect of OCDR principles and realizations that are possible in this case, reference is to be made to the following literature: WO2007065670 or Fercher et al., "Measurement of Intraocular Distances by Backscattering Spectral Interferometry", Opt. Comm. 117, 43.

The measuring apparatus 9 has an interferometer (not represented further in FIG. 1), and picks up components of the measurement beams 7 and 8 that are back-scattered out of the respective focus volume. In order to prevent the backscattering from being randomly a dark speckle, the measurement beam 7 is displaced laterally during the measurement of the scatter profile. i.e. during the acquisition of the A-scan measurement signal, such that the focus volume shifts, e.g. in the lens 4. This is symbolized by an arrow P in FIG. 1. To obtain the A-scan measurement signal, a multiplicity of scatter profiles, which represent A-scan individual signals, are acquired. The latter are also combined, in a manner to be described, to form the A-scan measurement signal.

Unlike the case of scanning used for imaging, such as that used, for example, in the case of optical coherence tomography (OCT), the lateral displacement of the focus is not synchronized to the recording of the radiation, i.e. of the A-scan individual signals. This absence of synchronization is manifested in that the lateral shift of the focus is not taken into account in the composition of the A-scan individual signals. In particular, the positional shift of the focus can be effected multiple times, or cyclically, around a central position, without the cycles being synchronized with the recording of the A-scan individual signals.

The shift is effected at a speed that is of such a magnitude that, during the period of time necessary for the pick-up of all A-scan individual signals of an A-scan measurement signal, the focus in the object shifts by at least half the focus diameter (preferably not more than 125 focus diameters), but wherein the shift preferably is subject to the above-mentioned limitations per period of radiation acquisition of the A-scan individual signals. This shifting of the focus diameter ensures that not all A-scan individual signals originate from the same speckle. A displacement of at least a focus diameter, it is prevented, with increased certainty that a destructively interfering object volume exclusively contributes to the measurement signal of an object structure, i.e. the non-presence of an object structure is prevented from being erroneously assumed at a particular axial position owing to destructive interference.

In a preferred variant, a maximum shift amplitude can be defined for the shift by the following Maximum shift amplitude[in lateral speckle diameters]=sqrt($R^2$−($R^2$−axial resolution)$^2$)/lateral resolution Thus, for the example already stated (posterior lens radius R=6 mm, lateral resolution 20 μm, axial resolution 20 μm), 24 lateral focus diameters are obtained as the maximum shift amplitude from the lens apex. If the maximum shift amplitude becomes greater, the axial position determination error owing to the lateral shift amplitude equals or exceeds that resulting from erroneous measurement at a dark speckle. Taking appropriate biometric application limits of 6 and 100 μm axial resolution and 10 to 20 μm lateral resolution, maximum shift amplitudes of 13 to 110 focus diameters from the lens apex are obtained.

If a statistical evaluation, to be explained in the following, is to be undertaken in order to derive information about the lens geometry, the maximum resolution must be significantly above the said values. It is thus expedient, in a first operating mode for length measurements, to maintain the said maximum shift amplitudes and, in a second operating mode for the determination of lens geometry, to effect greater shift amplitudes. The control device then changes between the two operating modes.

Figure 4A:
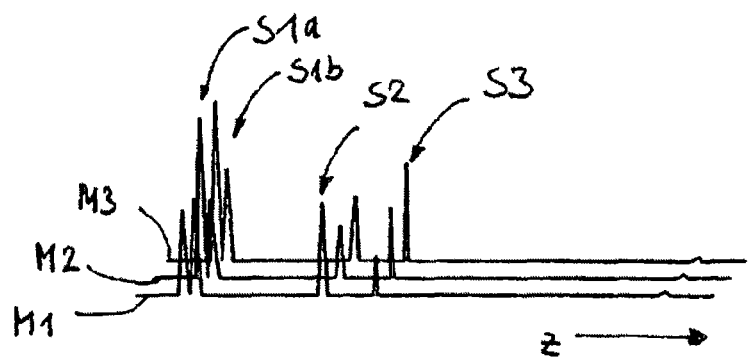
Figure 4B:
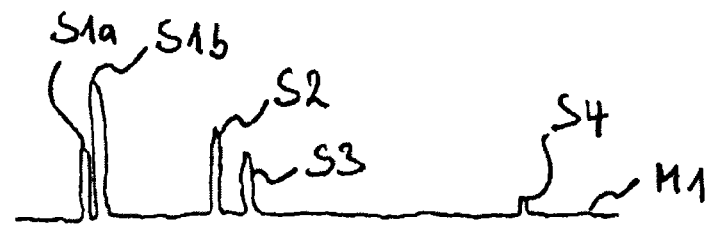
Figure 4B:
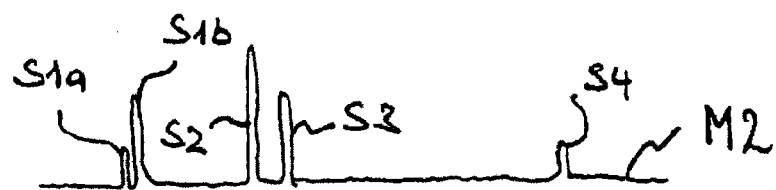
Figure 4B:
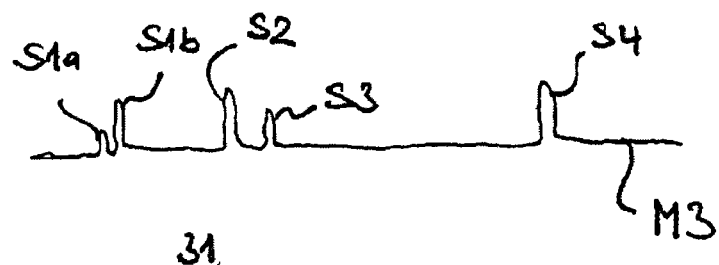

This effect is represented in FIG. 4b, which shows three A-scan individual signals M1, M2 and M3 in a perspectively staggered representation. The signals M1, M2 and M3 are plotted along the depth, i.e. along the z coordinate of the eye 1. As can be seen, the individual signals M1, M2 and M3 each have a plurality of peaks. Four peaks S1a, S1b, S2 and S3 are shown by way of example. The peaks S1a and S1b are caused by reflexes at the front side and back side, respectively, of the cornea 2. The peak S2 results from a reflex at the front side of the lens 4, the peak S3 from a reflex at the back side. As can be seen, all three perspectively staggered individual signals M1, M2 and M3 each show the peaks S1a, S1b, S2 and S3 on the same z coordinate, but with differing intensity. This difference in intensity is due to the fact that, owing to the lateral adjustment of the focus position (symbolized by the arrow P in FIG. 1), speckles of differing brightness have been acquired in the generation of the respective individual signal M1, M2 and M3, such that the scatter intensities vary. For example, the peak S3 of the individual signal M1 originates from a significantly darker speckle than does the peak S3 of the individual signal M3. For reasons of clarity in the representations (FIGS. 4a and 4b), peaks resulting from volume scattering, for example in the lens between S2 and S3, have been omitted, but the signal-improving aspects discussed in relation to the example of the speckles at the limiting surfaces clearly also apply to those from scattering volumina.

If the individual signals M1, M2 and M3 are added up to form the measurement signal, the latter has a significantly improved signal-to-noise ratio than a measurement with a fixed focus. The addition can be effected in various ways, for example by averaging. Selections of maxima can also be made, for example it is possible to select the peak S1a from the individual signal M2, the peak S1b from the individual signal M3, the peak S2 from the individual signal M1, and the peak S3 from the individual signal M3. For such selections, a person skilled in the art knows a great variety of approaches by which the signal-to-noise ratio can be further improved compared with an averaging.

FIG. 1 shows that the measuring apparatus 9 senses two differing regions of the eye 1, namely, the lens 4 and the retina 5 (the latter in the region of the fovea 6), and uses two separated measurement beams 7 and 8 for this purpose. This is effected for embodiments in which the measurement range that can be covered in the axial direction is not sufficient to simultaneously acquire two regions of the eye 1 that are of interest or the entire eye. In FIG. 1, the lateral displacement indicated by the arrow P is shown merely by way of example for one of the regions. Clearly, the measurement beam 8 can also be moved laterally in a corresponding manner.

On the other hand, in the case of a measuring apparatus 9 whose axial measurement depth is sufficient to acquire an object in the desired region in its entirety, a single measurement beam is used. The measurement region is then scanned appropriately. In the case of a TD OCDR, the reference arm length is appropriately adjusted in such a way that it covers, for example, the entire eye length. In the case of an SD OCDR system, analogously, the bandwidth of the spectral dispersion, or the spectral resolution, is to be selected accordingly and, in the case of an SS OCDR system, the bandwidth of the spectral tuning of the source is selected. Clearly, the second measurement beam can be omitted if an eye is not to be sensed in its entirety, but only a portion. This is the case on the eye 1 if, for example, the retina 5 or the lens 4 is not to be sensed. In order to optimize the signal intensities in this case, the focus is adjusted axially in the eye.

The effect of this adjustment is shown in FIG. 4b, which again shows three A-scan individual signals M1, M2 and M3, which are plotted along the depth, i.e. along the z coordinate of the eye 1. The designation of the peaks of the individual signals M1, M2 and M3 is analogous to that of FIG. 4a. As can be seen, in addition to the peaks S1a, S1b, S2 and S3 there is a further peak S4, which is caused by the backscattering at the retina of the eye. While the individual signals M1, M2 and M3 are being recorded, the focus is shifted in the direction of the retina, as a result of which the intensity of the peaks is altered. When the focus has a pronounced anterior position, as given for the individual signal M1, the peak S4 has only an extremely weak characteristic, whereas the peaks S1a and S2b are very high. By contrast, a pronounced posterior position of the focus emphasizes the peak S4.

If the individual signals M1, M2 and M3 are now again added up to form the measurement signal, the latter again has a significantly improved signal-to-noise ratio. Clearly, the above statements relating to FIG. 4a also apply analogously to FIG. 4b. Moreover, it is to be noted that, in both figures, the number of three individual signals has been selected purely for illustration. In fact, clearly, any number of individual signals can be used, and usually the number is significantly greater than three, e.g. some hundreds or thousands.

Figure 2:
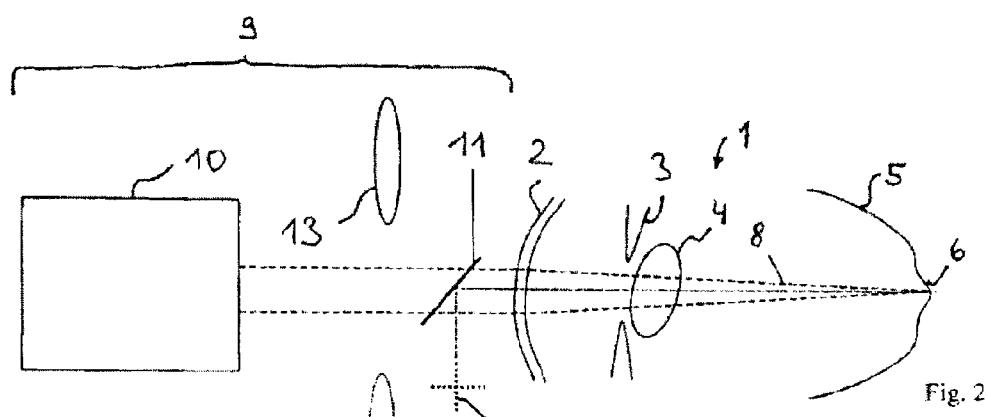
FIGS. 2 and 3 are more detailed representations of the apparatus of FIG. 1, FIGS. 4a and 4b depict signals obtained during operation of the apparatus of FIG. 1, FIG. 2 or FIG. 3, FIGS. 5 and 6 are a modification of the apparatus of FIGS. 2 and 3.
Figure 3:
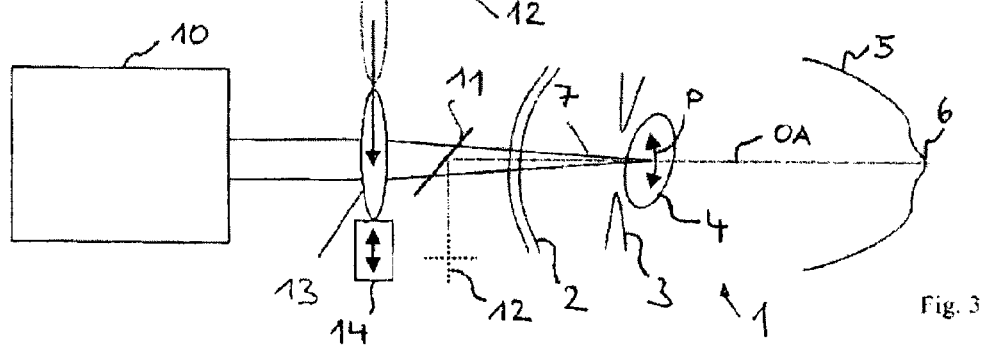

FIGS. 2 and 3 show, by way of example, a realization of the measuring apparatus 9 for the concept according to FIG. 1, in two differing operating states. In a first state, which is represented in FIG. 2, the measurement beam 8 is emitted by the measuring apparatus 9, which, by way of example, has an OCDR interferometer 10. In order to align the patient's eye 1 in such a way that the measurement beam 8 is incident on the fovea 6, a fixing image 12, upon which the patient fixes the gaze, is reflected in by means of a beam splitter 11. As a result, on the one hand, the patient aligns the eye 1 in such a way that the measurement beam 8 is incident on the fovea 6. At the same time, the fixing of the view to the fixation image 12 has the effect that the lens 4 is in a state that ensures that the focus of the measurement beam 8 is exactly positioned in the fovea 6.

The measuring apparatus 9 further has a lens or optical system 13 that can be swivelled into position, which swivelling into position causes the focus of the measurement beam to be located in the lens 4. Thus, in the state according to FIG. 3, the measurement beam becomes the measurement beam 7. The measurement beams 7 and 8 shown in FIG. 1 are thus realized sequentially by the apparatus, i.e. not simultaneously. Of course, as explained later, simultaneous emission of both measurement beams 7 and 8 can also be effected.

The measuring apparatus 9 further has a positioning drive 14 for the lens 13, which positioning drive adjusts the position of the inserted lens transversely in relation to the optical axis OA of the measuring apparatus 9. As a result, the position of the focus shifts laterally in the lens 4, as indicated by the arrow P. The displacement of the lens 13 perpendicularly to the optical axis is clearly only one of many possibilities for laterally shifting the focus. Other optical elements can also be used for this purpose, e.g. deflection mirrors, one or more plane-parallel plates that can be tilted differently, etc.

A modification of the design of FIG. 3 with respect to variation of the polarization state of the measurement beam 7 optimizes the intensity of the measurement radiation that is back-scattered from an object location in the eye 1. In this design, the lens 13 and the positioning drive 14 are replaced by a device for altering the polarization state of the measurement beam. The polarization state is varied in a manner analogous to the focus position during the measurement, such that, as a result, the A-scan measurement signal is composed of A-scan individual signals that have been obtained with differing polarization states of the measurement beam. Thus, the variation of the polarization state replaces the alteration of the position of the focus in this embodiment. Otherwise, the statements made here also apply in their entirety to this variant.

Figure 5:
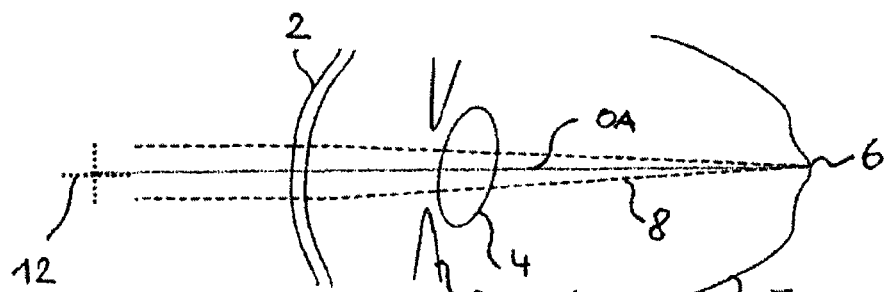
Figure 6:
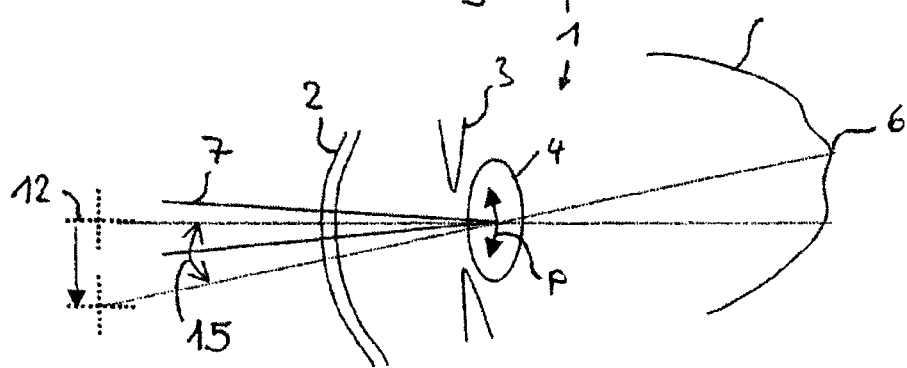

FIGS. 5 and 6 show an approach in which no optical components of the measuring apparatus 9 need be moved. Shown schematically in FIG. 5 is a state similar to that of FIG. 2, wherein elements such as the beam splitter 11 and other components of the measuring apparatus 9 have been omitted for reasons of clarity. The lateral shift of the focus is now effected, not by moving an element of the measuring apparatus 9 that images the measurement beam 7 or 8 into the eye 1, but by displacing the fixation image 12. This causes the patient to refix the view during the recording of the measurement signal and, as a result, the focus of the measurement beam 7 shifts laterally in the lens 4.

The patient tilts his eye, and therefore his axis of vision by an angle 15, causing the position of the focus of the measurement beam 7 in the lens 4 to be shifted.

The lateral shift of the position of the focus during the measurement also causes a variation in the alignment of the measurement beam in relation to any curved boundary surfaces in the eye, e.g. the lens 4. It is thereby possible to achieve strong back-scatterings having predominantly specular components that, for example, have not been achieved by means of a rough preadjustment or that have been lost again as a result of an intermediate relative movement of the measuring apparatus and the object, e.g. an eye movement. These signal improvements through shifting of the position of the focus of the measurement beam during the measurement are particularly assisted by a refixing, i.e. a displacement of the fixing image 12, in particular in distance measurements in which boundary surfaces of the lens 4 are relevant, since the optical axis of the lens 4 is usually tilted relative to the axis of vision of the eye.

Figure 7:
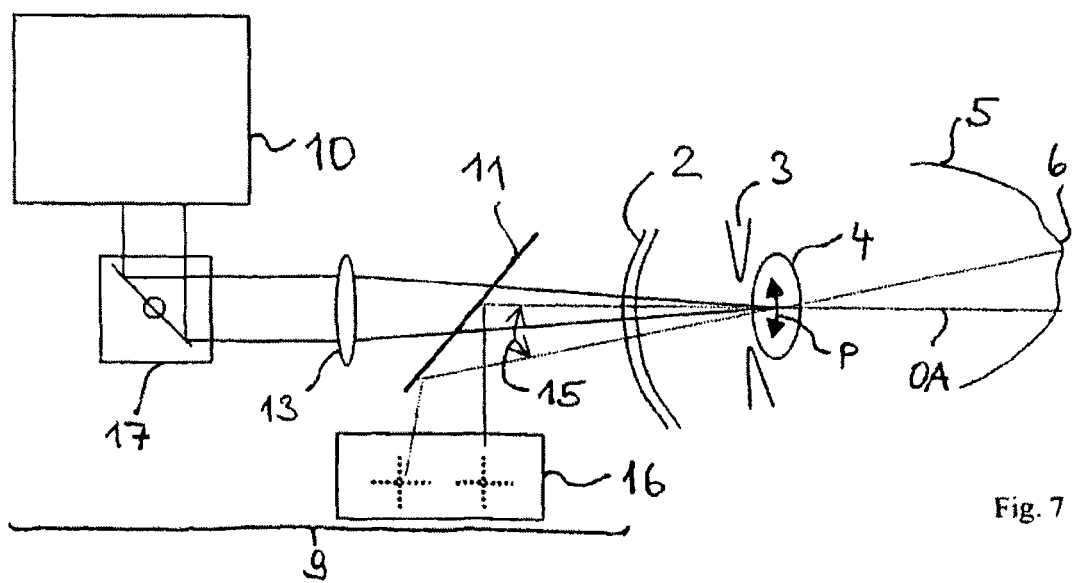
FIG. 7 is a more detailed representation of the apparatus of FIGS. 5 and 6.

FIG. 7 shows an embodiment for the measuring apparatus 9 for realizing the positional shifting according to the principles previously described. Elements of the measuring apparatus 9 of FIG. 7 that correspond to those of FIGS. 2 and 3 are denoted by the same references and, to avoid repetitions, are not described over again. To enable the focus to be shifted, a fixation image device 16 is provided to generate the fixing image 12, which fixation image device can generate a fixing pattern, e.g. the cross represented in FIG. 7, at differing locations, e.g. by means of a corresponding display element on which the fixing pattern can be displaced. It is then possible to dispense with a transversal displacement of the lens 13 and with the corresponding drive 14. This is not intended to mean, however, that the lens 13 cannot be swivelled out of the beam path, as in FIG. 2, in order to generate the measurement beam 8.

Further, also present in the design according to FIG. 7 is a deflection mirror 17, which can be used to lateral shift of the focus in addition to the lateral shift of the focus achieved by the refixing, in particular for the purpose of reducing the speckle modulation of the signal.

Figure 8:
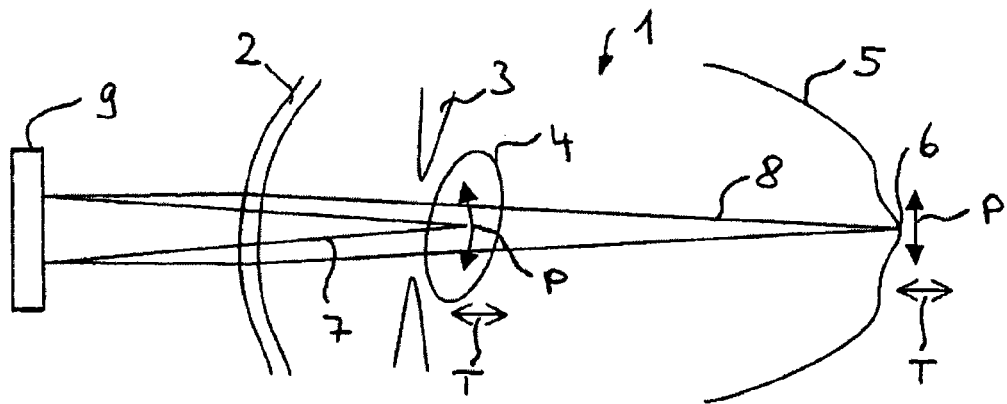
FIG. 8 is a further modification of the apparatus of FIG. 1.
Figure 9:
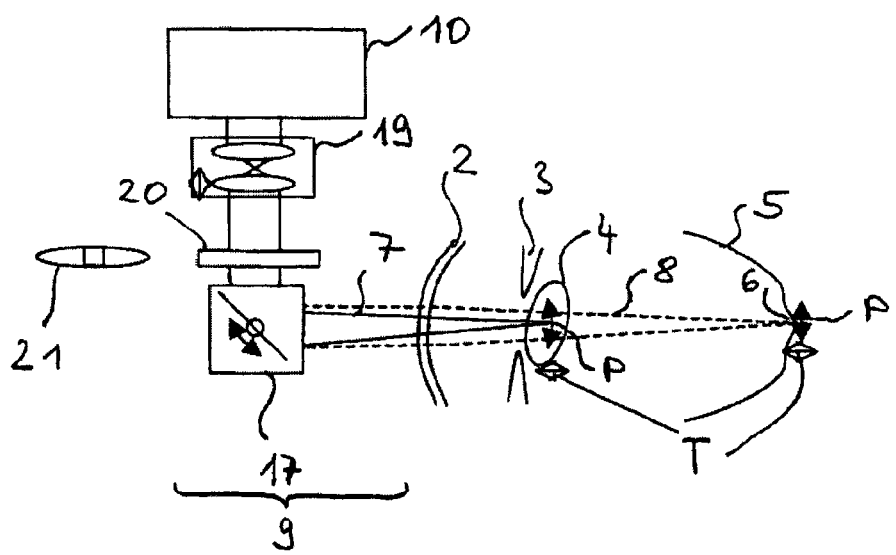
FIG. 9 is a more detailed representation of a further design of the apparatus of FIG. 1.

FIGS. 8 and 9 relate to embodiments in which two regions of the object, thus of the eye 1 in the embodiment example, are acquired simultaneously. The measurement beams 7 and 8 are emitted simultaneously and focussed into the lens 4 and onto the retina 5, respectively. The focus is shifted, as mentioned, while the radiation for the A-scan signals for the two regions is being collected, i.e. one measurement signal for each region. In this case, on the one hand, the focus shift is effected laterally, in that the deflection mirror, which was stationary in the design according to FIG. 7, is now designed so as to be pivotable. Its movement provides for the lateral shift of the focus of both the measurement beam 7 and the measurement beam 8. This is represented by the two arrows P in FIG. 8.

In addition, in the design according to FIG. 9, an axial shift of the focus is also effected. Provided for this purpose is an adjustable optical system 19 having a displaceable lens that simultaneously shifts the foci of the measurement beams 7 and 8 along the optical axis. This is symbolized by an axial measurement range T in FIG. 9. In contrast with that which was explained with reference to FIG. 4*b*, the axial shift of the focus is thus not effected over a large distance, in order to optimize the back-reflexes from differing boundary surfaces that are spaced apart axially, but in the design according to FIG. 9 is effected over a distance which is small in relation to the measurement depth. This shift, as also the lateral shift, has the advantage of preventing a dark speckle from resulting in an unwanted reduction of the measurement signal. The design according to FIG. 9 is thus an example of the fact that the lateral shift of the focus and the axial shift of the focus can also be combined. Further, the design according to FIG. 9 is an example of the fact that the axial shift of the focus (of course even without lateral shift of the focus) can also be effected, in principle, over a region that is small against the spacing of the distances to be determined.

In principle, TD, SS or SD approaches can be used in the design according to FIG. 9, as also in the other embodiments. Corresponding designs for the measuring apparatus 9 are also known to a person skilled in the art.

FIG. 9 shows, by way of example, further details of the measuring apparatus 9, which, however, can also be used in different ways. In order to generate the measurement beams 7 and 8 simultaneously, the measuring apparatus 9 has, after the interferometer 10, a correspondingly splitting element, e.g. a diffractive optical element (DOE) 20 or a segmented lens 21, shown by way of example on the left, next to the DOE. The splitting element generates the differently focussed double measurement beam 7, 8.

Figure 10:
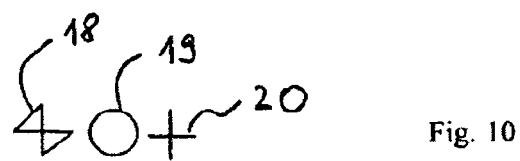
FIG. 10 depicts fixing patterns that can be used in the operation of one of the apparatuses.

The patterns 18, 19 and 20 represented in FIG. 10 are fixing patterns, which can be generated, in the case of a deflection mirror 17 that can be adjusted on two axes, to serve as a fixing image. For this purpose, a measurement beam is used that can still be seen by a patient at least with low sensitivity, for example in the spectral range 700 . . . 850 nm or, if invisible measurement radiation is used (for example 1060 nm), a visible fixation beam (for example 635 nm) is superposed before the deflection device 17, for example by means of a dichroic beam splitter (not shown).

Figure 11:
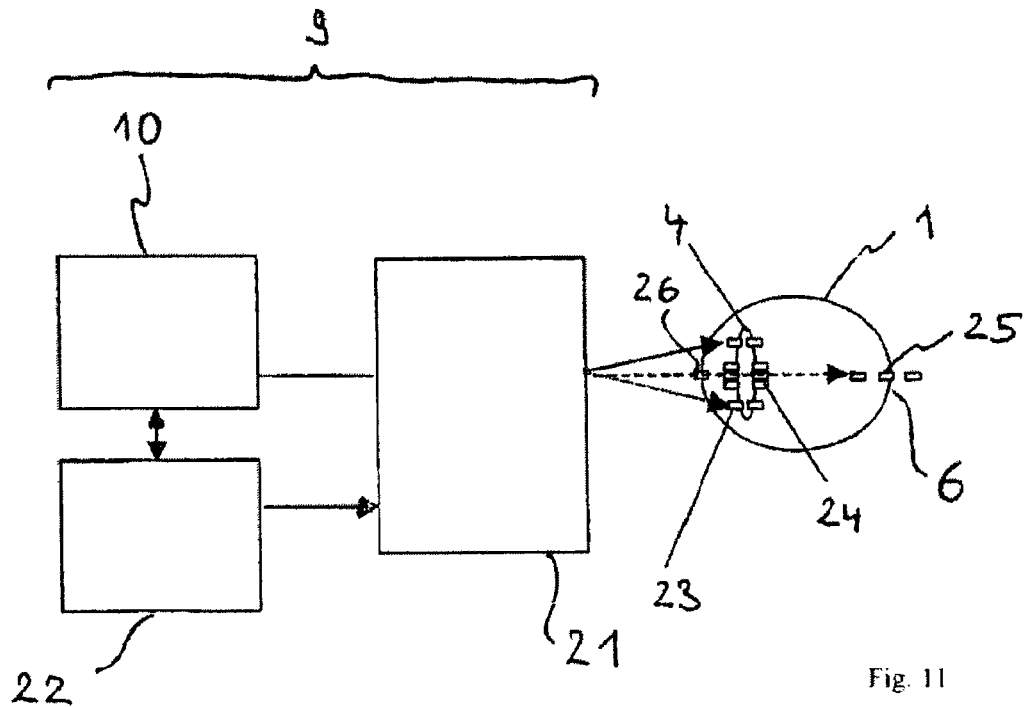
FIG. 11 is a further variant of the apparatus of FIG. 1.

The shift of the focus, which generally constitutes a shift of the focus position, can also be effected according to the embodiment of FIG. 11 by a programmable optical system 21, which executes particular pre-defined, i.e. programmed, alterations in respect of lateral focus position, axial focus position, focus size, polarization state or number of foci. Explained as an alteration in the following is a shift of the focus, both laterally and axially. This, however, is to be understood as being purely exemplary. The programmable optical system executes a program of focus adjustments. In this case it is activated accordingly by a control device 22. The arrow drawn for the control device 22 of the measuring apparatus 9 between the control device 22 and the programmable optical system 21 in FIG. 11 is intended to indicate that the control device 22 merely, for example, switches the programmable optical system 21 on and off, but in any case does not input or read out any information about the current program state of the programmable optical system—this because the control device 22 does not make any use of the current focus shift (or polarization variation) in the generation of the A-scan measurement signals, or of the A-scan individual signals.

The programmable optical system 21 shifts the position of the focus in the eye 1 to the locations symbolized by small boxes in FIG. 11. The focus is thus located at various locations on the anterior surface 23 of the lens 4, at various locations on the posterior surface 24 of the lens, at a location in the region of the corneal vertex 26 and at a plurality of locations in the region of the retina 25. The duration of each program step is preferably of a sufficient length of time to enable at least one A-scan individual signal to be recorded, wherein, however, this recording is not effected in synchronism with the program steps. Thus, there may well be A-scan individual signals present which were recorded while the programmable optical system changed from one program step to the next.

It is to be emphasized here once again that the shift of the focus position does not serve primarily to cover a larger measurement range required for measuring distances or partial distances in the eye. Rather, the measurement range is covered through corresponding configuration of the interferometer 13. Thus, depending on the approach (TD, SD or SS OCDR), the interferometer is tuned, the spectral composition of the measurement radiation is varied or a spectrum of the interference radiation is recorded. Also, the shifting of the focus position does not serve to generate image information through scanning transversely in relation to the main direction of incidence of the radiation but, rather, is intended to provide A-scan individual signals that each sense differing regions of the eye with differing sensitivity and, following combination of the A-scan individual signals which combination results in an A-scan measurement signal having a significantly improved signal-to-noise ratio. However, differences between the individual A-scans can be evaluated statistically, for example in order to obtain information about shape and position, without recourse to synchronization and imaging.

Figure 12:
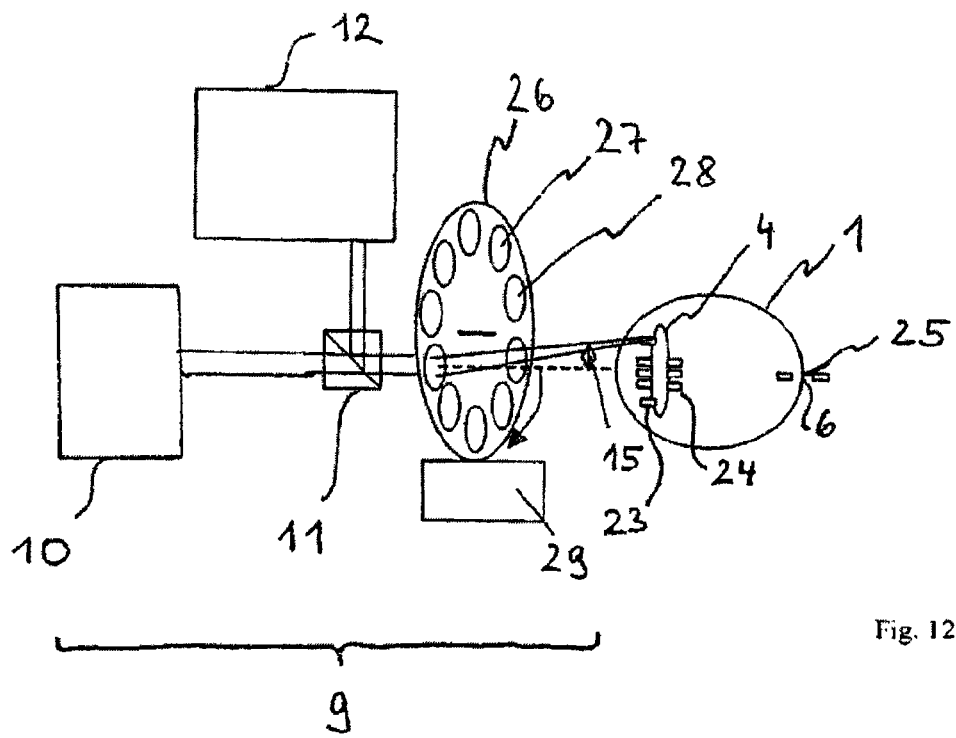
FIG. 12 is a more detailed representation of the apparatus of FIG. 11.

FIG. 12 shows by way of example a possible realization of the programmable optical system. Here, it is realized as a lens wheel 26 which comprises various optical systems or lenses 27, 28 (etc.) that focus the incident beam from the interferometer 10 onto the differing sites. A drive 29 causes the lens wheel 26 to rotate in the direction of the arrow represented in FIG. 12, such that the individual optical systems 27, 28 etc. are successively rotated into the beam path. An example of the lenses that can be used for the optical systems 27, 28 etc. are wedge-shaped lenses having differing radii, which effect not only an axial focus shift (base of differing focal length), but also a lateral focus displacement.

Instead of the lens wheel, the programmable optical system 22 can clearly also comprise deformable and/or tiltable mirrors or lenses, so-called liquid-crystal spatial light modulators (LC SLM), which are controlled by a suitable pattern memory and/or pattern generator. The programmable optical system 21 can be adjusted in a stepwise manner or even continuously. In the latter case, transition phases from one program step to the next, e.g. with an instantaneous decentring of the optical system, can also be used to average out speckles from predominantly volume scattering structures such as, for example, the volume of the cornea 2 or of the lens 4.

As already mentioned, the combining of the A-scan individual signals can be effected in various ways. The combining can also be made to be dependent on depth. Thus, a maximum value selection can be provided in the region of the lens 4 and an averaging provided in the region of the retina 25. Further, FIG. 12 also shows the insertion of the fixing image 12 via the beam splitter 11. If the fixation stimulus effected thereby is disturbed by the programmable optical system 21, the fixation can also be coupled-in after the programmable optical system or, alternatively, blocked by means of appropriate filters before the programmable optical system. Owing to the comparatively rapid sequence of the program steps, the fixation image is switched off for individual program steps, since this is not perceptible by a patient.

As already mentioned, the shifting of the focus position, or the change in polarization, is not effected in synchronism with the pick-up of the A-scan individual signals, but is preferably effected sufficiently slowly, in relation to the recording of an A-scan individual signal, such that, for example, more than half of the recorded A-scan individual signals are acquired with a substantially unchanged focus position/polarization state.

Figure 13:
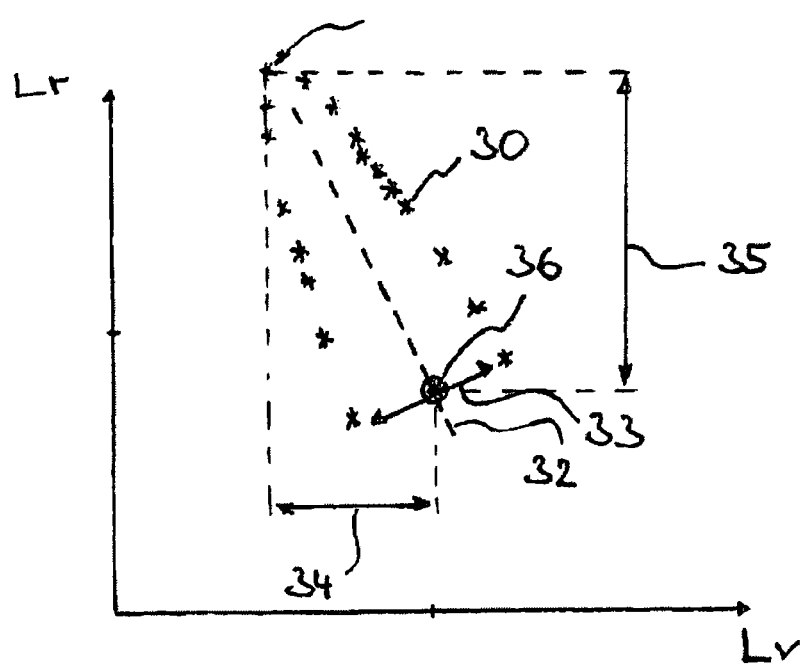
FIG. 13 is a diagram for evaluation of the A-scan signals.

The control device that measures the desired partial distance in the eye from the A-scan measurement signals thus does not use the current state of the polarization adjustment or focus position shift. Nevertheless, as already discussed, it is possible to obtain additional information about the geometry of the eye lens 4 (also referred to as the crystalline lens) from an evaluation of the signals. This is represented in FIG. 13. The parameters that can be determined are, for example, the tilt of the lens 4, the thickness of the lens 4 and the radii of the posterior surface and anterior surface of the lens 4. These items of information can also be obtained through an evaluation of the A-scan individual signals. Each A-scan individual signal provides a position Lv of the anterior lens surface and a position Lr of the posterior lens surface. Each such measurement is then plotted in a diagram, as shown by FIG. 13. In FIG. 13, each star 30 symbolizes a pair of ascertained positions of the anterior lens surface and of the posterior lens surface, which originates from an A-scan individual signal.

The position Lr of the posterior lens surface is plotted on the vertical axis, the position Lv of the anterior lens surface 23 being plotted on the horizontal axis.

The plotted pairs 30 result in a symmetrical curve, which lies symmetrically in relation to a symmetry axis 32.

The pair 31, for which the maximum difference between Lv and Lr is obtained, automatically indicates the thickness of the lens, since the lens thickness is clearly obtained from the most anterior position Lv of the lens anterior surface 23 and the most posterior position Lr of the anterior lens surface 24.

The opening of the curve, i.e. the maximum distance 33 of two points relative to the symmetry axis, is a measure of the tilt of the lens. The tilt of the lens is therefore determined from the opening of the curve in relation to the symmetry axis 32. The tilt of the lens is equal to the angular distance between an optical axis and an axis of vision of the eye, or the angle of the lens equatorial plane relative to the axis of vision.

The distance between the vertex of the resultant curve and an intersection point 36 obtained perpendicularly to the symmetry axis 32 for the points at greatest distance from the symmetry axis 32 is denoted by 34 in FIG. 13, and is proportional to the inverse radius of the anterior lens surface 23 and to the maximum lateral distance of the focus points.

This applies, analogously, to the distance, denoted by 35, between the vertex 31 and the intersection point 36, which distance is proportional to the inverse radius of the posterior lens surface 24 and to the maximum lateral distance. By knowing the maximum lateral distance, the radius of the anterior lens surface and of the posterior lens surface can therefore be determined from the quantities 35 and 34. An appropriate characteristics diagram, for example, previously generated from experimental data, can be employed for this purpose. It is to be emphasized once again that, for this analysis, it is not necessary to know when the focus was at which location. For the analysis described, it is merely necessary to know which pairs 30 of Lv and Lr occurred in the A-scan individual signals, but not when, or in which A-scan individual signal.

The approach can also be applied to post-operative measurement of lens implants (IOL) for checking the lens shape and position, and also to the measurement of the corneal radii, for example for the purpose of determining Gullstrand ratios. The cornea, after all, also corresponds to a lens having curved surfaces, wherein, however, the sign of the posterior radius of curvature is changed relative to that in the case of the eye lens. As a result, the curve, represented in FIG. 13, in the case of a corneal measurement appears to be mirrored vertically, but can be evaluated analogously.

FIGS. 15 to 18 present alternative arrangements according to the invention of polarization-optical (use of a polarization-optical, double-refracting optical system for object illumination) or diffraction-optical (use of a diffraction-optical, double-refracting optical system for object illumination) parallel FD short-coherence interferometry.

Figure 15:
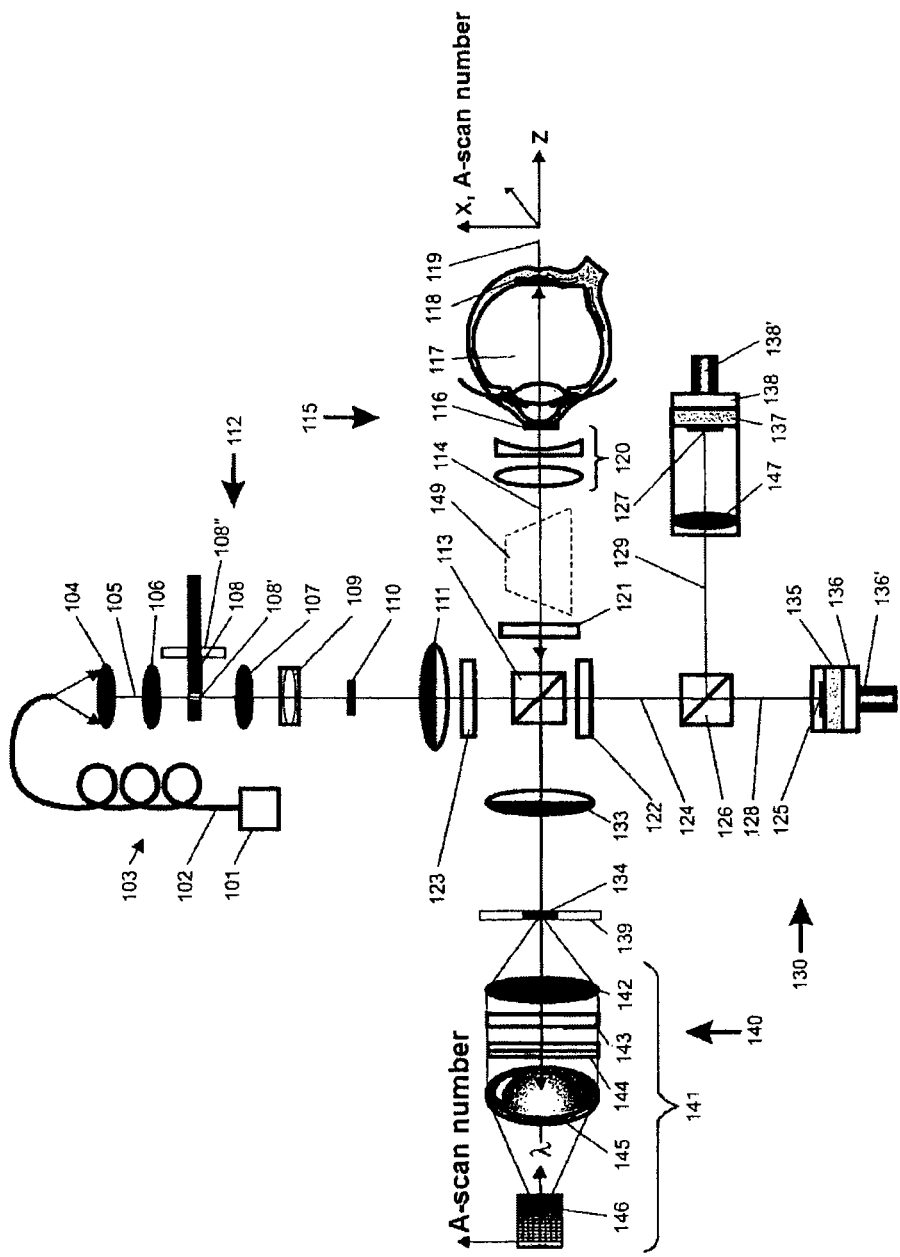
FIG. 15 is a further embodiment of the invention with a double-refracting optical system.

FIG. 15 shows a beam path according to the invention which uses a polarization-optical, double-refracting optical system (111) for the simultaneous acquisition of two measurement fields. Reference 101 denotes a light source having a short coherence length but full spatial coherence, for example a superluminescent diode or a laser operating in broadband, transversal mono-mode. A light-conducting fibre 102 conducts the light emitted from 101 through a polarization controller 103 to a collimation optical system 104. A light beam 105 emerging from the latter illuminates a Michelson interferometer. An optical system 106 and an optical system 107 together constitute a telecentric optical-system pair, in the common focal plane of which is located an opening 108' of a chopper 108 that rotates about its axis 108". The chopper 108 defines the exposure times for a CCD array 146. The optical system 107 collimates the light beam, which diverges behind the chopper, back to a parallel beam 105. The latter is incident upon a cylindrical optical system 109 having a horizontal cylinder axis, and is focussed by the latter into a line focus 110. The line focus 110 is imaged by the double-refracting optical system 111 into two differing image distances. The double-refracting optical system 111 can be realized either by means of polarization optics or by means of diffractive optics.

The beam path of FIG. 15, which beam path is based on polarization optics, uses polarization-optical, double-refracting lenses. Such lenses can be realized from crystals of two differing double-refraction types (positive and negative), wherein their crystal axis is located in the lens plane. In the example of negatively double-refracting calcite (refractive index of the ordinary ray $n_o$>refractive index of the extraordinary ray $n_{ao}$), as material for a double-refracting lens, light oscillating in the plane of the crystal axis undergoes greater refraction than light oscillating perpendicularly in relation to the crystal axis. In the case of positively double-refracting crystals, such as quartz, the light oscillating in the plane of the crystal axis undergoes less refraction than light oscillating perpendicularly in relation to the crystal axis. For two light waves oscillating perpendicularly in relation to one another, therefore, a double-refracting lens has two differing focal lengths. In the following, it is assumed that the crystal axis of 111 is oriented perpendicularly in relation to the plane of projection, and that the lens material is calcite. An imaging of the line focus 110 into two differing image distances is controlled here by means of the polarization controller 103. This controller can be used to set the oscillation plane of the light in the illumination beam 105 in such a way, for example at 45° to a plane of projection, that this light has both a component that is parallel to and a component that is perpendicular to the crystal axis of the double-refracting optical system 111. These two components, oscillating perpendicularly in relation to one another will image the line focus 110—according to the associated image distances of the double-refracting optical system 111—into differing image distances.

A measurement beam 114 is constituted by the imaging rays reflected at a beam splitter 113. The measurement beam 114 generates in a measurement arm 115, respectively, an image 116 of the line focus 110 in the entrance pupil of an eye and an image 118 in the fundus of the eye 117. For this purpose, the double-refracting optical system 111, for example in the case of negatively double-refracting calcite being used, is designed in such a way that the ordinary part of the beam 105 generates an image 116 at a location of an optical axis 119 where the eye is to be positioned with its entrance pupil. Further, the double-refracting lens 110 can be set up and dimensioned in such a way, for example, that the extraordinary part of the beam 105 first images the line focus 110 to infinity, such that it is imaged in a relaxed emmetropic eye on the retina. In the case of ametropic eyes, the line focus, initially imaged to infinity, can be imaged onto the retina with the aid of a zoom optical system 120 that compensates the defective vision.

It is advantageous to optimize the adaptation of the measurement beam intensities, in the two light beams realizing the images of the line focus, to the reflectivities, of differing strength, of the eye structures of interest. Through setting of the oscillation plane in the beam 105 by means of the fibre-optic polarization controller 103 relative to the optical crystal axis of the optical system 111, the splitting of the intensities to the components can be adjusted, both parallelwise and perpendicularly in relation to the crystal axis. Alternatively, this can also be effected by rotating the polarization plane by means of rotatable polarizers or a λ/2 plate, for example located between the optical systems 104 and 106.

A reference arm 130 having a reference beam 124 is constituted by the imaging rays from an illumination arm 112 that are transmitted from the beam splitter 113. In the reference arm, also, the double-refracting optical system 111 generates a respective image of the line focus 110 in differing image distances. A beam splitter 126 further splits the reference beam 124 into a reference beam part 128, adapted to the measurement arm length in relation to the entrance pupil of the eye, and a reference beam part 129, having an optical system 147 arranged at a distance of its focal length in front of a reflector 137. The reference beam part 129 is adapted to the measurement arm length in relation to the fundus of the eye. The reference mirrors 135 and 137 (with optical system 147) are mounted on electrically controllable positioning tables 136 and 138 having positioning motors 136' and 138'. (In each of the two reference arms there is also produced a second line focus image, which, however, is ultimately imaged onto the slit 139 in a defocused manner and is thus suppressed).

A further optimization is achieved through a flexible allocation of the beam intensities to the interferometer measurement arm 115 and interferometer reference arm 130, in that 113 is realized as a polarization beam splitter and a rotatable λ/2 plate 123 is placed before it. Rotation of the λ/2 plate allows the balance of the intensities in the measurement arm 115 and reference arm 130 to be altered continuously.

An optimization through reduction of the light losses at the measurement arm and reference arm can be achieved at the polarization beam splitter 113 through λ/4 plates 121 and 122 (at 45° to the plane of projection). If these λ/4 plates are oriented such that they generate circularly polarized light, for outgoing and returning light from the respective interferometer arms (115 and 130) they cause the oscillation plane to be rotated by 90°. The light coming back from the measurement arm 115 is transmitted, without reflection losses, through the polarization beam splitter 113 into the spectrometer arm 140, the light coming back from the reference arm 130 is transmitted, without transmission losses, through the polarization beam splitter 113 into the spectrometer arm 140.

In the spectrometer arm 140, double-refracting optical system 133 generates secondary representations 134 of images 116, 118, 125 and 127 of the line focus 110. If the optical systems 111 and 133 have the same focal lengths and are arranged symmetrically around the splitter plane of the beam splitter 113, a particularly clear case exits: The secondary images of images 116, 118, 125 and 127 are produced in the same size at the same location 134. At the location of a secondary line focus image 134 is an entrance slit 139 (rectangular opening, drawn folded into the plane of projection) of the spectrometer 141. This entrance slit eliminates parasitic light components reflected out of the interferometer.

A collector optical system 142 of the spectrometer images the secondary line focus image via a diffraction grating 144, by means of a spectrometer optical system 145, onto the two-dimensional detector array 146. This analyzer can also be realized so as to be rotatable, which provides for further adaptation of the intensities of the interferometer beams. The diffraction grating disperses the secondary line focus image in a wavelength-dependent manner along the λ coordinate of the two-dimensional detector array 146.

Figure 16:
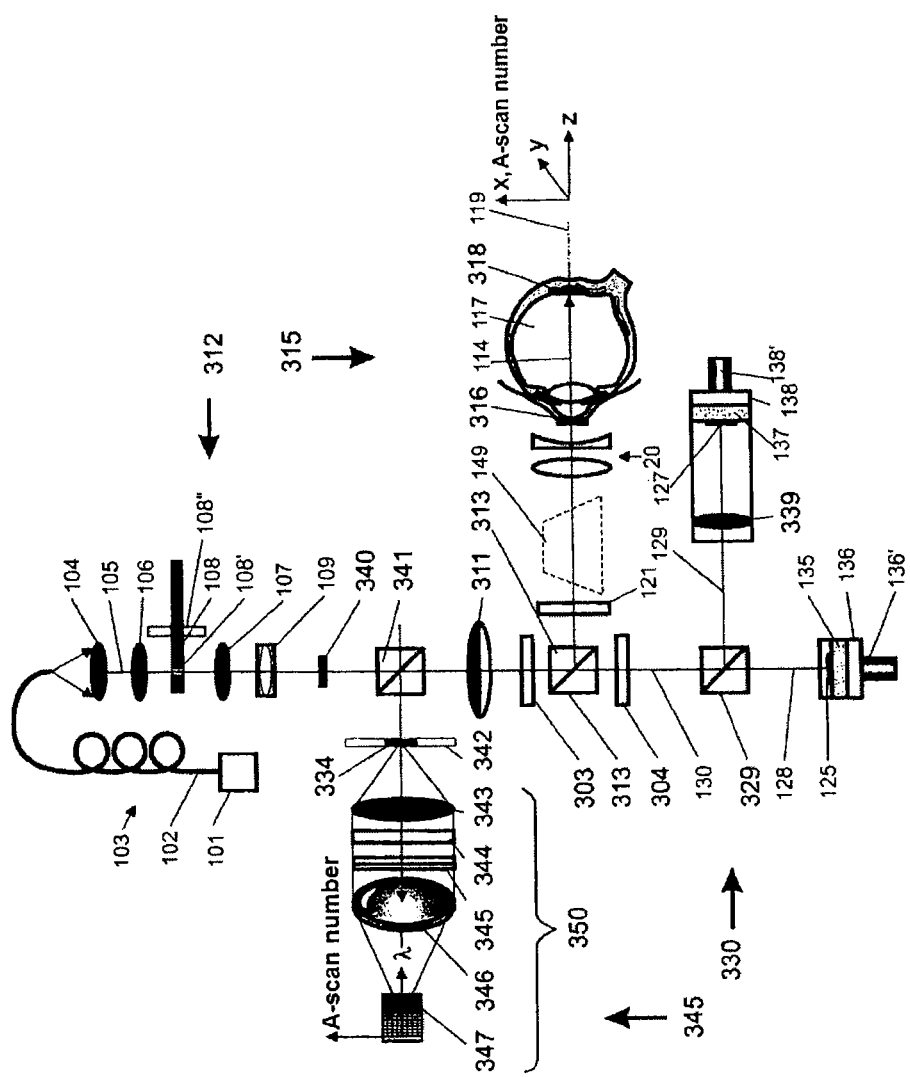
FIG. 16 is a further embodiment of the invention with a diffractive optical system.
Figure 17:
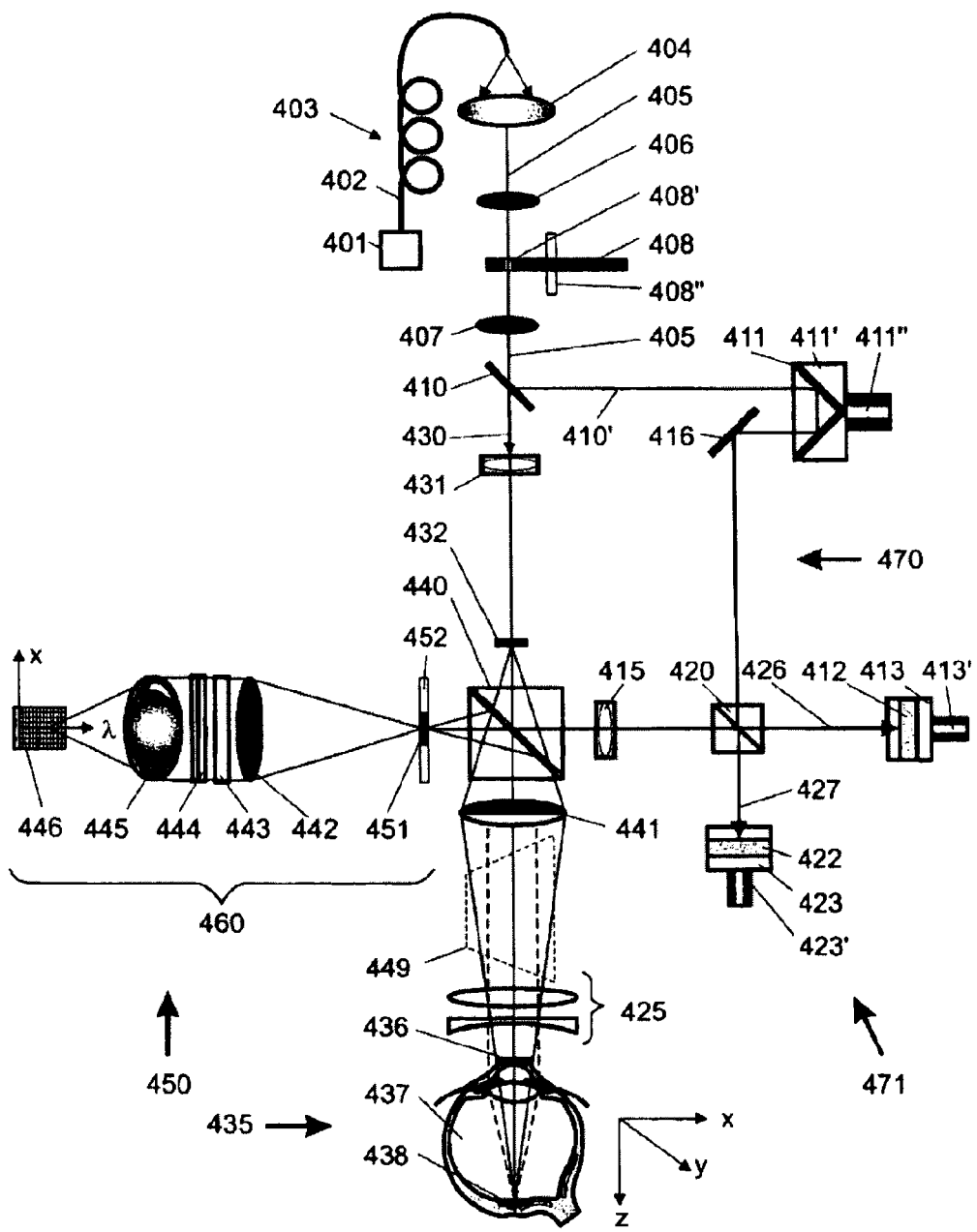
FIG. 17 is a modification of the embodiment from FIG. 15.
Figure 18:
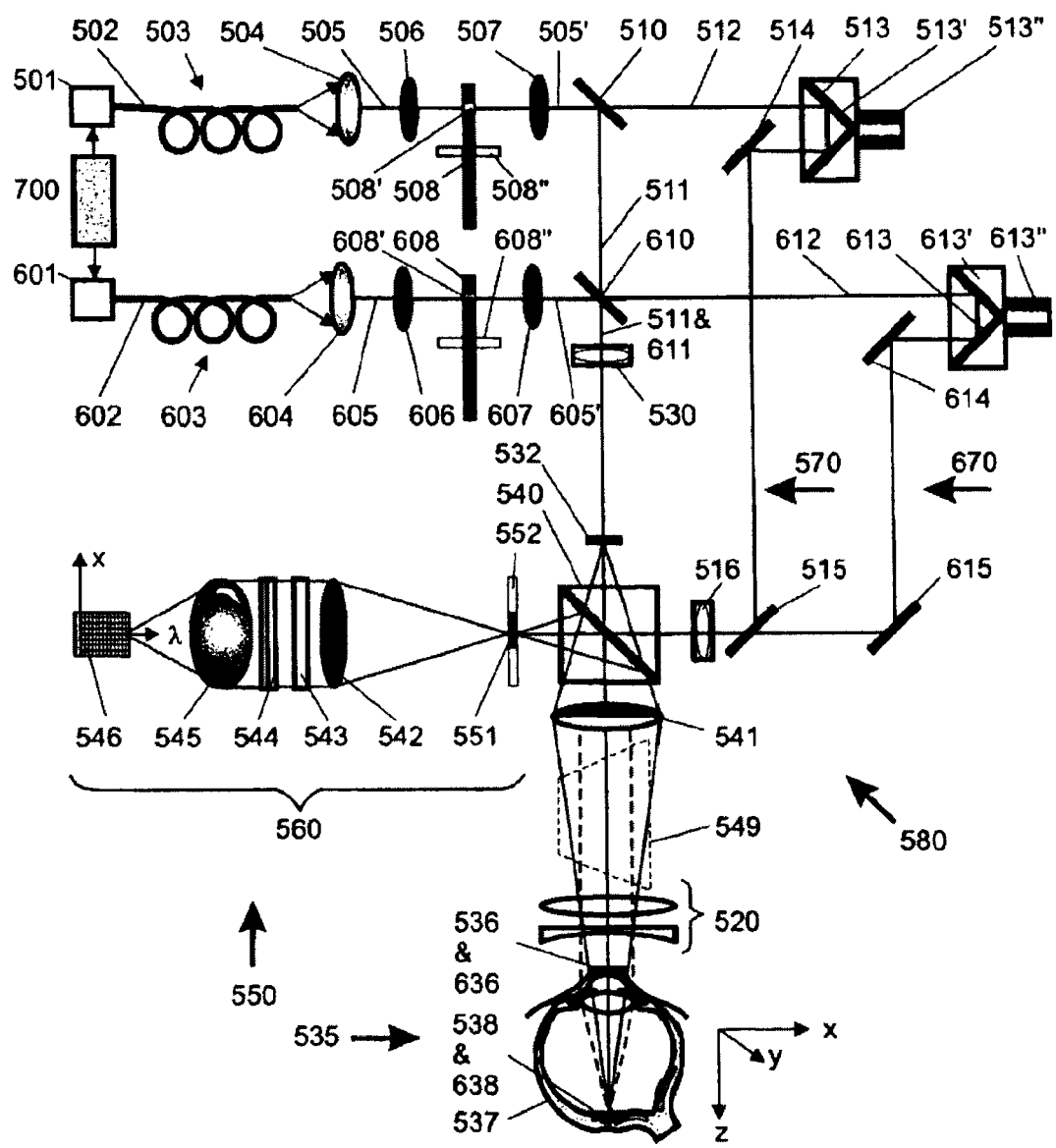
FIG. 18 is a further embodiment of the invention with two FD short coherence interferometers.

The direction of diffraction is directed out of the plane of projection; the spectrometer optical system 145 and the detector array 146 are therefore—also in FIGS. 16, 17 and 18—indicated as being tilted downwards about a horizontal axis, out of the plane of projection. The scan number of FIG. 14 corresponds here to the x coordinate in the eye. The depth structure along the z coordinate is thus obtained simultaneously—for A-scans that are adjacent in the transversal direction, from the spectrum of the associated interferometer signal as an input data set, by means of a FT. The arrangement outlined in FIG. 15 has the advantage that there is only one beam splitter 113 between the eye and the detector. This makes it easy to eliminate its sensitivity-limiting effect. A disadvantage, on the other hand, is the requirement for the polarization-optical, double-refracting refractive optical systems 111 and 133, because the latter are based on the use of uncommon materials (for example, calcite), which are difficult to machine with high precision or are difficult to purchase.

Otherwise, instead of the polarization-optical, double-refracting optical systems 111 and 133, diffractive, double-refractive optical systems having the corresponding focal lengths can also be used in the beam path according to FIG. 15. Owing to the low optical quality of double-refracting optical systems, however, it is generally appropriate not to use these more frequently than is absolutely necessary.

FIG. 16 presents an alternative according to the invention, which, for the purpose of simultaneously acquiring two measurement fields, is based on the use of a single double-refracting element, here a diffractive double-refracting optical system.

As in FIG. 15, in the beam path of FIG. 16, likewise, the item 101 is a light source having a short coherence length but full spatial coherence, for example a superluminescent diode or a laser operating in broadband, transversal mono-mode. The light-conducting fibre 102 conducts the light emitted from 101 through the polarization controller 103 to the collimation optical system 104. The fibre-optic polarization controller 103 allows rotation of the polarization plane of the light beam in the interferometer and, consequently, in the case of use of a polarization beam splitter 313, an optimization of the light distribution between the measurement beam 114 and the reference beam 130. The light beam 105 emerging from the collimation optical system 104 illuminates the interferometer. The optical system 106 and the optical system 107 together constitute a telecentric optical-system pair, in the common focal plane of which is located the opening 108' of the chopper 108 having the axis of rotation 108". The chopper 108 defines the exposure times for the CCD array 347. The optical system 107 collimates the light beam, which diverges behind the chopper 108, back to a parallel beam. The latter is incident upon the cylindrical optical system 109, and is focussed by the latter into a line focus 340. After the line focus 340, the light beam 105 passes through a beam splitter 341. The line focus 340 is imaged by a double-refracting optical system 311 into two differing image distances. Here, the double-refracting optical system 311 is a diffractive optical system (but can also be a polarization-optical optical system).

Diffractive optical systems can have a plurality of focal lengths. (Their values depend on the radial spatial frequency of the Fresnel lenses and Fresnel phase plates used in these optical systems). Here, preferably, a diffractive optical system (311) having only two focal lengths is used. Further focal lengths would only divert the light, unused, out of the beam path. Accordingly, the line focus 340 is imaged into two differing image distances.

The measurement beam is constituted by the imaging rays reflected by a beam splitter 313. These imaging rays generate in a measurement arm 315, respectively, an image 316 of the line focus 340 in the entrance pupil of the eye 117 and an image 318 in the fundus of the eye. For this purpose, the double-refracting optical system 311 is designed in such a way that a first diffracted part of the beam 105 generates the image 316 at a location of the optical axis 119 where the eye is to be positioned with its entrance pupil. Moreover, the double-refracting optical system 311 is set up and dimensioned in such a way that the second diffracted part of the beam 105 first images the line focus 340 to infinity, such that 340 is imaged in a relaxed emmetropic eye on the retina (318).

In the case of ametropic eyes, the line focus, initially imaged to infinity, can be imaged with the aid of a zoom optical system 120 that compensates the defective vision.

The reference arm 330 is constituted by the imaging rays from the illumination arm 312 that are transmitted from the beam splitter 313. In the reference arm, also, the double-refracting optical system 1311 generates a respective image of the line focus 340 in differing image distances. A beam splitter 329 further splits the reference beam 130 into a partial reference beam 128, adapted to the measurement arm length in relation to the entrance pupil of the eye, and a partial reference beam 129, adapted to the measurement arm length in relation to the fundus of the eye. The reference mirrors 135 and 137, and likewise an optical system 339, whose focal length corresponds to its distance from the reference mirror 137, are mounted on electrically controllable positioning tables 136 and 138 having positioning motors 136' and 138'. (Here also, in each of the two reference arm parts there is also produced a second line focus image, which, however, is ultimately imaged onto the slit 139 in a defocused manner and is thus suppressed).

In the spectrometer arm, the double-refracting optical system 311 generates secondary representations 334 of the images 316, 318, 125 and 127 of the line focus 340. These secondary images of the images 316, 318, 125 and 127 are produced in the same size at the same location 334. At the location of the secondary line focus image 334 is an entrance slit 342 (rectangular opening, drawn folded into the plane of projection) of the spectrometer 350. This entrance slit eliminates parasitic light components reflected out of the interferometer. A collector optical system 343 of the spectrometer 350 images the secondary line focus image further via a diffraction grating 345 and by means of a spectrometer optical system 346 onto a two-dimensional detector array 347. Reference 344 denotes an analyzer, which ensures optimal interference capability of the associated measurement and reference light beams. The diffraction grating 345 disperses the line focus image on the detector array 347 in a wavelength-dependent manner along the A coordinate. Here also, the scan number of FIG. 14 corresponds to the x coordinate in the eye. Here, as also according to the arrangement of FIG. 15, all spectra for the A-scan interferometer signals that are adjacent in the x direction are obtained simultaneously. These constitute the input data set for the FT for calculation of the depth structure along the z coordinate.

The requirements, listed above, for obtaining optimal signals are approached differently by the arrangements described: while the arrangement according to FIG. 15 uses two double-refracting optical systems and one beam splitter, the arrangement according to FIG. 16 manages with one double-refracting optical system, but requires two beam splitters between the eye and the spectrometer. While beam splitters always result in light losses and/or an additional resource requirement to prevent the latter, high-quality double-refracting optical systems are difficult to produce and are expensive. From this aspect, more favourable interferometers produce beam paths from combinations of Mach-Zehnder and Michelson interferometer arrangements, as represented in FIGS. 17 and 18, wherein the Mach-Zehnder part constitutes the illumination and the reference arm of the Michelson interferometer.

FIG. 17 shows a short-coherence interferometry arrangement having only a single beam splitter between the eye and the spectrometer. The beam path is a short-coherence interferometer having a Mach-Zehnder-like reference beam path having an optical extension for the purpose of path length adaptation. Reference 401 is a light source having a short coherence length but full spatial coherence, for example a superluminescent diode or a laser operating in broadband, transversal mono-mode. A light-conducting fibre 402 conducts the light emitted from 401 through a polarization controller 403 to a collimation optical system 404. A light beam 405 emerging from the latter illuminates the interferometer. An optical system 406 and an optical system 407 together constitute a telecentric optical-system pair, in the common focal plane of which is located an opening 408' of a chopper 408 that rotates about its axis 408". The chopper 408 defines the exposure times for a CCD array 446. The optical system 407 collimates the light beam, which diverges behind the chopper, back to a parallel beam 405. The latter is incident upon a beam splitter 410, which reflects off a first reference beam 410'. The part of the beam 405 which passes a beam splitter 420 constitutes a measurement beam 430 and is incident upon the cylindrical lens 431 having a cylinder axis that is assumed here to be horizontal, which cylindrical lens focuses the measurement beam into a horizontal line focus 432.

The light beam diverging vertically from the line focus 432 passes through a beam splitter 440 and is imaged by a double-refracting optical system 441 into two differing image distances. As already described in connection with the examples of FIGS. 15 and 16, this double-refracting optical system can be realized, either by means of polarization-optical, double-refracting lenses or by means of diffractive, double-refracting optical systems, such that the measurement beam 430 generates in a measurement arm 435, respectively, an image 436 of the line focus 432 in the entrance pupil of an eye and an image 438 in the fundus of the eye 437. In the case of ametropic eyes, the line focus, initially imaged to infinity, is imaged the fundus by the aid of a zoom optical system 425 that compensates the defective vision.

The light reflected from a line focus images 436 and 438 is reflected by a double-refracting optical system 441, via the beam splitter 440, into a spectrometer arm 450 and, in the case of a polarization-optical double-refracting optical system, generates two secondary images at a location 451. In the case of a diffractive double-refracting optical system 441, both primary images 436 and 438 each produce two secondary images, i.e. a total of four images are produced; of these four images, however, only two are focussed at the location 451, while the other two are imaged in a defocused manner there, thus can be largely suppressed by means of a slit aperture 452 of the spectrometer (whose rectangular opening is indicated as folded into the plane of projection) that is set up there.

Reference beams and measurement beams subsequently constitute a Mach-Zehnder-like interferometer: The reference beam 410' is reflected out of the beam 405 by the beam splitter 410 and is incident upon an optical extension constituted by 410, 411 and 416: A retroreflector 411 is mounted on a sliding table 411' and driven by a motor 411". A 90° mirror 416 reflects the reference beam onto a Michelson interferometer 471 positioned in a corner of a Mach-Zehnder interferometer 470. The beam splitter 420 divides two reference beams 426 and 427. Reference mirrors 412 and 422 are mounted on electrically controllable positioning tables 413 and 423 having a positioning motor 413' and having a positioning motor 423', which allow the optical path lengths of these reference beams to be altered steplessly relative to one another. Reference beams 426 and 427 reflected from the reference mirrors are incident upon a cylindrical lens 415, which focuses it through the beam splitter 440 into the line focus 451 in the spectrometer arm 450.

The line focus 451 (now constituted by a total of four beams) is now located in the entrance pupil of a spectrometer 460 having an entrance slit 452. A collector optical system 442 of the spectrometer images the secondary line focus image via a diffraction grating 444 by means of the spectrometer optical system 445 onto a two-dimensional detector array 446. Reference numeral 443 denotes an analyzer, which ensures the interference capability of the various measurement and reference beams. The diffraction grating disperses this line focus image in a wavelength-dependent manner along the λ coordinate of the detector array. The x coordinate of the detector array 446 corresponds to the x coordinate in the eye and the scan number of FIG. 14. The depth structure along the z coordinate is thus obtained simultaneously—for adjacent A-scans from the spectrum of the associated interferometer signal as an input data set, by means of FT.

The beam splitter 410 can also be omitted, and the reference beams can be obtained by means of the portion of the measurement beam reflected at the beam splitter 440. The cylindrical lens 415 must be set up virtually to the mirror surface of the beam splitter 440, at a distance of its focal length from the line focus 432. The reflectors 411 and 416 are then also omitted. However, the intensities of the reference beams are then no longer fully independent of those of the measurement beams.

FIG. 18 presents a short coherence interferometry beam path of, at the same time, two short coherence FD interferometers in one: Two separate light sources 501 and 601, having a short-coherence length but full spatial coherence, such as superluminescent diodes or lasers operating in broadband, transversal mono-mode, illuminate two separate Mach-Zehnder beam paths 570 and 670 in a partially common arm. Both beam paths come out in a Michelson interferometer 580 where, finally, they illuminate the same measurement object and a common spectrometer arm 550.

A light-conducting fibre 502 (602) conducts the light emitted from short coherence light sources 501 (601) through a polarization controller 503 (603) to a collimation optical system 504 (604). Reference 700 denotes an electric power supply of the light sources 501 and 601 that can be controlled externally, for example by a PC. A light beam 505 (605) illuminates the interferometer. An optical system 506 and 606 and optical systems 507 and 607 together constitute telecentric optical-system pairs, in the common focal plane of which are located openings 505' and 608' of choppers 508 and 608 that rotate about their axes 508" and 608". These choppers define the exposure times for a CCD array 546. The optical systems 507 and 607 collimate the light beam, which diverges behind these choppers, back to parallel beams (505' and 605'). The latter are incident upon beam splitters 510 and 610, which split these beams into measurement beams 511 and 611 and reference beams 512 and 612.

The two measurement beams 511 and 611 are focussed by a double-refracting optical system 530 into a line focus 532. The two light beams now diverging (vertically) from the line focus 532 pass through a beam splitter 540 and are imaged by a double-refracting optical system 541 into two differing image distances. As already described in connection with the above examples, this double-refracting optical system can be realized, either by means of polarization-optical, double-refracting lenses or by means of diffractive, double-refracting optical systems, such that measurement beams 511 and 611 generate, respectively, an image 536 and 636 of the line focus 532 in the entrance pupil of an eye 537 and, respectively, an image 538 and 638 in a fundus of the eye 537. In the case of ametropic eyes, the line focus, initially imaged to infinity, can be imaged onto the fundus with the aid of a zoom optical system 520 that compensates the defective vision.

The light reflected from the line focus images 536, 636 and 538 and 638 is reflected by the double-refracting optical system 541, via a beam splitter 540, into a spectrometer arm 550 and, in the case of a polarization-optical double-refracting optical system 541, generates two secondary images at a location 551. In the case of a diffractive double-refracting optical system 541, both primary images 536 and 538 each produce two secondary images, i.e. a total of four images are produced; of these four images, however, only two are focussed at a location 551, while the other two are imaged in a defocused manner there, thus can be largely suppressed by means of the slit aperture 552 of the spectrometer (whose rectangular opening is indicated as folded into the plane of projection) that is set up there.

The parts of the beams 505 and 605 transmitting the beam splitters 510 and 610 constitute the reference beams.

The reference beam 512 transmitted at the beam splitter 510 is incident upon an optical extension composed of a roof-edge mirror 513 and a 45° mirror 515. The roof-edge mirror 513 is mounted on an electrically controllable positioning table 513' having a positioning motor 513", which allows the optical path length of the reference beam 512 to be altered in a stepless manner. This reference beam 512 is reflected, via the 45° beam splitter 515, to a cylindrical lens 516, which focuses it through a beam splitter 540 into a line focus 551.

A reference beam 612 transmitted at a beam splitter 610 likewise is incident upon an optical extension, composed of the beam splitter 610, a roof-edge mirror 613 and a 45° mirror 614. The roof-edge mirror 613 is mounted on an electrically controllable positioning table 613' having a positioning motor 613". This reference beam is reflected, via the 45° beam splitter 615, to the cylindrical lens 516, which focuses it through the beam splitter 540 into the line focus 551 in the spectrometer arm 550.

In the case of measurement of the axial length of the eye, the optical path differences of the reference beams in relation to the measurement beams are set, for example, such that in each case a separate measurement field of the corneal region entrance pupil and a measurement field of the fundus can be imaged.

The line focus 551 now constituted by two measurement beams and two reference beams is located in an entrance pupil of a spectrometer 560 having the entrance slit 552. A collector optical system 542 of the spectrometer images the secondary line focus image via a diffraction grating 544, by means of a spectrometer optical system 545, onto a two-dimensional detector array 546. Reference 543 is an analyzer, which ensures the interference capability of these beams. The diffraction grating disperses this line focus image in a wavelength-dependent manner along the A coordinate of the detector array. The x coordinate of the detector array 546 corresponds to the x coordinate in the eye and the scan number of FIG. 14. By means of a FT, the depth structure along the z coordinate is thus obtained—simultaneously—for a plurality of adjacent A-scans from the spectrum of the associated interferometer signal, as an input data set.

The advantage of this arrangement, which, however, requires two light sources, is that both measurement fields can be configured entirely independently of one another. Through corresponding setting of the optical lengths of the reference beams by means of the optical extensions, the two measurement fields can also be positioned in any way, and differing wavelengths can also be used to optimize the penetration depths into the eye, and the two measurement fields can be electrically switched off and on very rapidly by means of the electric power supply 700 for the purpose of signal identification, or modulated in their brightness and with differing frequencies and signal shapes. The optimizations already described in connection with FIG. 15 can also be performed in the arrangements according to FIGS. 16, 17 and 18: Thus, for example, in the case of the double-refracting optical systems 441 and 541 based on polarization optics, the intensities of the two measurement beams can be varied relative to one another by means of the polarization controller.

Figure 14:
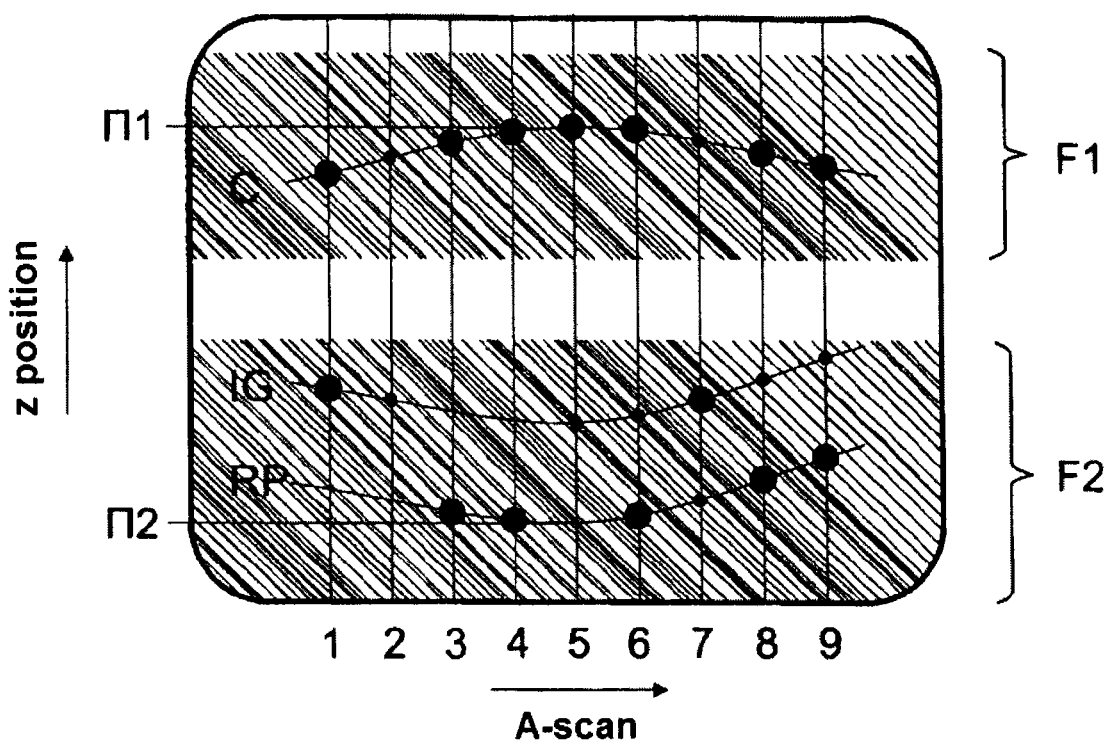
FIG. 14 is a representation of various A-scan signals.

As mentioned above, two measurement fields are realized at differing depths by means of the two reference beams. These measurement fields occur simultaneously as a result of the FT of the spectrometer signal. There arises therefore the problem of identifying and distinguishing the signals of the two measurement fields. There are two possibilities for this. The standard method consists, as already mentioned, in setting differing optical path differences between the associated line foci in the measurement and reference beams, thus here, for example, as outlined in FIG. 17, between light from 436 and the light beam 426, on the one hand, and between light from 438 and the light beam 427, on the other hand. The associated measurement fields are then reconstructed in differing z positions, as represented in FIG. 14.

This strategy is not always successful; for example, it fails frequently in the initial phase of a measurement, when first reconstructed A-scan signals first have to be found through corresponding positioning of the proband. For this purpose, it is advantageous to be able to identify the individual A-scan signals. This can be achieved in various ways. For example, periodic harmonic movement of a reference mirror (125 or 127 in the arrangements of FIGS. 15 and 16) or of the optical extensions in the arrangements of FIGS. 17 and 18, through corresponding control of the associated drives, can be used to achieve a periodic movement of the reconstructed A-scan signals along the z position (FIG. 14). Instead of a harmonic movement, anharmonic movement patterns, for example sawtooth-type patterns, can be used to identify the A-scan signals. In addition to stated simple periodic movement of a mirror, both reference mirrors can also be moved in opposing directions or with differing periods. Finally, the one or the other A-scan signal can also be rendered invisible through very rapid movement.

In the case of diseases in the fovea region or at the corneal surface, it can be appropriate to alter the azimuthal orientation of the line focus in the eye. This can be achieved through the use of image rotators such as, for example, a Dove prism (149, 449, 549) or other reversion prisms, such as the Abbe-König prism, the Schmidt-Pechan prism, or the Uppendahl prism reversal system, consisting of three prisms, in front of the eye.

It is also to be mentioned that, instead of the polarization controller in all arrangements, it is also possible to use in the illumination arm, for example after the collimation optical systems (104, 404, 504, 604), rotating λ/2 plates after an appropriately oriented polarizer, and other methods belonging to the state for the art for rotating the polarization plane of a light beam.

Finally, the interpretation of the eye structures on which the length measurements are based can be further improved in that the cumulative A-scan signals are obtained from simple A-scans that are offset parallelwise in relation to one another and that are distributed in a transversally extensive region (in x and y direction). The methods, described above, of averaging on two-dimensional regions are thereby extended to three dimensions. Further, the Dove prism (149, 449 and 549) mentioned in all arrangements can also be used to obtain three-dimensional OCT images from an anterior eye region (for example, the anterior chamber) and a posterior eye region (for example, the retina). Corresponding measurement data sets in the three-dimensional space can be obtained along straight lines with differing azimuthal orientations perpendicular to the eye axis if this prism is used to rotate the eye relative to the interferometer (virtually) into differing azimuthal orientations. In the case of the Dove prism, for example, a simple rotation device is sufficient for this purpose, which rotates this prism about a parallel to the hypotenuse surface; the image in this case is rotated by double the angle. Similarly, other reversion prisms, such as the Abbe-König prism, the Schmidt-Pechan prism or the Uppendahl prism reversal system, consisting of three prisms, can also be used for this purpose.

The invention claimed is:

1. An apparatus for performing measurements on an eye, including measuring a depth of an anterior chamber, a lens thickness, a corneal thickness, retinal layer thicknesses or an axial length, wherein the apparatus comprises
   an interferometer that focuses at least one measurement beam into the eye along an optical axis at a focus, collects back-scattered radiation and interferometrically generates a measurement signal indicating structures of the eye by time-domain, spectral-domain or Fourier-domain coherence reflectometry;
   an adjustment device that laterally and/or axially shifts the focus in the eye or varies a polarization state of the measurement beam;
   a control device that controls the interferometer, wherein the control device generates a plurality of A-scan individual signals from the back-scattered radiation and combines the plurality of A-scan individual signals to form an A-scan measurement signal, the control device controlling the adjustment device that shifts the position of the focus or varies the polarization during collection of the back-scattered radiation from which the control device generates the A-scan individual signals; and
   wherein the back-scattered radiation contributes to the A-scan measurement signal in a plurality of differing positions of the focus or in a plurality of differing polarization states of the measurement radiation.

2. The apparatus according to claim 1, wherein the control device combines the plurality of A-scan individual signals to form the A-scan measurement signal without taking into account the control or an operating state of the adjustment device.

3. The apparatus according to claim 1, wherein the control device controls the adjustment device such that, during collection of the back-scattered radiation the position of the focus in the eye shifts by at least half of a focus diameter.

4. The apparatus according to claim 1, wherein the control device, in combining the A-scan individual signals to form the A-scan measurement signal, selects and weights the separate A-scan individual signals according to signal characteristic thereof.

5. The apparatus according to claim 1, wherein the control device controls the adjustment device during collection of the back-scattered radiation to cyclically adjust the position of the focus around a central position.

6. The apparatus according to claim 1, wherein the adjustment device comprises a fixation image device, which is connected to the control device and presents a fixation image to a patient to align the eye, wherein the fixation image device displaces the presented fixation image to laterally shift the position of the focus of the measurement beam in the eye.

7. The apparatus according to claim 1, further comprising a driven, positionally adjustable optical element located in a beam path of the measurement beam, wherein a positional adjustment of the optical element displaces the position of the focus of the measurement beam in the eye.

8. The apparatus according to claim 1, wherein the driven, positionally adjustable optical element comprises a displaceable lens.

9. The apparatus according to claim 1 wherein a lateral shift of the position of the focus is effected at a shifting speed that is less than the quotient of half of a focus diameter and a duration of collection of the back-scattered radiation required for an A-scan individual signal.

10. A computer implemented method for performing measurements on an eye, including measuring a depth of an anterior chamber, a lens thickness, a corneal thickness, retinal layer thicknesses or an axial length, comprising:
   focusing at least one measurement beam into the eye along an optical axis;
   collecting back-scattered radiation;
   generating a measurement signal using an interferometer indicating structures of the eye interferometrically by time-domain, spectral-domain or Fourier-domain coherence reflectometry; and
   shifting the position of the focus in the eye laterally and/or axially or varying a polarization state of the measurement beam;
   generating a plurality of A-scan individual signals interferometrically from the back-scattered radiation and combining the plurality of A-scan individual signals to form an A-scan measurement signal;
   wherein the shifting of the position of the focus or the variation of the polarization state is performed during collection of the back-scattered radiation from which the plurality of A-scan individual signal are generated, and wherein back-scattered radiation contributes to the A-scan measurement signal in a plurality of differing positions of the focus or in a plurality of differing polarization states of the measurement radiation.

11. The method according to claim 10, further comprising combining the plurality of A-scan individual signals to form the A-scan measurement signal without the shifting of the position of the focus or the variation of the polarization state being taken into account.

12. The method according to claim 10, further comprising shifting the position of the focus by at least half of a focus diameter during collection of the back-scattered radiation.

13. The method according to claim 10, further comprising in the combining of the A-scan individual signals to form the A-scan measurement signals, selecting and weighing the separate A-scan individual signals according to signal characteristics thereof.

14. The method according to claim 10, further comprising cyclically adjusting the position of the focus around a central position during collection of the back-scattered radiation.

15. The method according to claim 10, further comprising presenting a fixation image to a patient to align the eye and displacing the fixation image laterally, shifting the position of the focus of the measurement beam in the eye.

16. The method according to claim 10, further comprising driving a positionally adjustable optical element, in a beam path of the measurement beam and adjusting the positionally adjustable optical element to shift the position of the focus of the measurement beam in the eye.

17. The method according to claim 16 further comprising making the positionally adjustable optical element a displaceable lens.

18. The method according to claim 10, further comprising effecting a lateral shift of the position of the focus a shifting speed that is less than the quotient of half of a focus diameter and a duration of collection of the back-scattered radiation required for an A-scan individual signal.

19. The method according to claim 10, wherein the thickness of an eye lens of the eye is determined from the A-scan individual signals or from a plurality of A-scan measurement signals and further comprising determining a position of an anterior lens surface and posterior lens surface for all signals, and calculating the difference between a most anterior of the determined positions of the anterior lens surface and a most posterior of the determined positions of the posterior lens surfaces and taken as the thickness of the eye lens.

20. The method according to claim 10, further comprising plotting several pairs of a determined position of an anterior lens surface and a determined position of a posterior lens surface in a diagram, wherein the determined positions of the anterior lens surface are plotted along one diagram axis and the determined positions of the posterior lens surface are plotted along the other diagram axis, and combining or interpolating the thus obtained points to form a curve, and evaluating a shape of the curve in respect of position and shape of an eye lens to determine parameters of the eye lens of the eye.

21. The method according to claim 20, further comprising determining a maximum distance of the curve or of the obtained points from a symmetry axis of the curve, and determining a measure for the tilt of the eye lens relative to the axis of vision of the eye on basis of the maximum distance.

22. The method according to claim 20, further comprising obtaining a measure for an anterior lens radius from a greatest lateral focus shift used and determining a maximum distance between a curve vertex and a maximum of anterior lens positions by the evaluation of the shape of the curve.

* * * * *

UNITED STATES PATENT AND TRADEMARK OFFICE
CERTIFICATE OF CORRECTION

PATENT NO. : 8,534,838 B2
APPLICATION NO. : 13/059039
DATED : September 17, 2013
INVENTOR(S) : Roland Barth et al.

It is certified that error appears in the above-identified patent and that said Letters Patent is hereby corrected as shown below:

On title page 2, item (56) References Cited – FOREIGN PATENT DOCUMENTS

Delete reference "DE 10 2007 052 828" and insert --DE 10 2007 052 858--

Signed and Sealed this
Tenth Day of December, 2013

Margaret A. Focarino
*Commissioner for Patents of the United States Patent and Trademark Office*